(12) United States Patent
Tanamachi et al.

(10) Patent No.: US 7,910,798 B2
(45) Date of Patent: Mar. 22, 2011

(54) TRANSGENIC ANIMALS EXPRESSING CHIMERIC ANTIBODIES FOR USE IN PREPARING HUMAN ANTIBODIES

(75) Inventors: Dawn M. Tanamachi, San Carlos, CA (US); Peter Brams, Sacramento, CA (US); Amelia Black, Los Gatos, CA (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 12/295,557

(22) PCT Filed: Mar. 30, 2007

(86) PCT No.: PCT/US2007/008231
§ 371 (c)(1),
(2), (4) Date: Jan. 28, 2009

(87) PCT Pub. No.: WO2007/117410
PCT Pub. Date: Oct. 18, 2007

(65) Prior Publication Data
US 2009/0260093 A1    Oct. 15, 2009

Related U.S. Application Data

(60) Provisional application No. 60/744,104, filed on Mar. 31, 2006.

(51) Int. Cl.
*A01K 67/027* (2006.01)
*C12P 21/08* (2006.01)
*C07H 21/04* (2006.01)

(52) U.S. Cl. .................... 800/18; 800/6; 536/23.53
(58) Field of Classification Search .................. 800/18, 800/6; 536/23.53
See application file for complete search history.

(56) References Cited

U.S. PATENT DOCUMENTS

| | | |
|---|---|---|
| 4,474,893 A | 10/1984 | Reading |
| 4,634,666 A | 1/1987 | Engleman et al. |
| 4,714,681 A | 12/1987 | Reading |
| 4,803,167 A | 2/1989 | Haber et al. |
| 5,001,065 A | 3/1991 | Larrick et al. |
| 5,104,674 A | 4/1992 | Chen et al. |
| 5,175,384 A | 12/1992 | Krimpenfort et al. |
| 5,204,244 A | 4/1993 | Fell et al. |
| 5,416,260 A | 5/1995 | Koller et al. |
| 5,434,340 A | 7/1995 | Krimpenfort et al. |
| 5,512,282 A | 4/1996 | Krivan et al. |
| 5,530,101 A | 6/1996 | Queen et al. |
| 5,545,806 A | 8/1996 | Lonberg et al. |
| 5,545,807 A | 8/1996 | Surani et al. |
| 5,565,354 A | 10/1996 | Ostberg |
| 5,567,610 A | 10/1996 | Borrebaeck et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,633,425 A | 5/1997 | Lonberg et al. |
| 5,653,977 A | 8/1997 | Saleh |
| 5,661,016 A | 8/1997 | Lonberg et al. |
| 5,690,933 A | 11/1997 | Cobbold et al. |
| 5,698,196 A | 12/1997 | Matsushima et al. |
| 5,702,946 A | 12/1997 | Doerschuk et al. |
| 5,721,367 A | 2/1998 | Kay et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 6,023,010 A | 2/2000 | Krimpenfort et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,255,458 B1 | 7/2001 | Lonberg |
| 6,300,129 B1 | 10/2001 | Lonberg et al. |
| 6,596,541 B2 | 7/2003 | Murphy et al. |
| 6,673,986 B1 | 1/2004 | Kucherlapati et al. |
| 7,041,871 B1 | 5/2006 | Lonberg et al. |
| 7,501,552 B2 * | 3/2009 | Lonberg et al. .................. 800/6 |
| 2002/0086014 A1 | 7/2002 | Korman et al. |
| 2005/0153394 A1 | 7/2005 | Black |
| 2006/0015957 A1 * | 1/2006 | Lonberg et al. ................. 800/18 |

FOREIGN PATENT DOCUMENTS

EP    0 315 062    5/1989
(Continued)

OTHER PUBLICATIONS

Butler (1998) Revue Scientifique et Technique Office International Des Epizooties. vol. 17, No. 1, 43-70.*
Abbas et al., Cellular and Molecular Immunology, W.B. Saunders Company, Philadelphia, PA, 90-92, 1991.
Adra et al., "Cloning and expression of the mouse pgk-1 gene and the nucleotide sequence of its promoter," Gene 60(1): 65-74, 1987.
Albertsen et al., "Construction and characterization of a yeast artificial chromosome library containing seven haploid human genome equivalents," Proc. Natl. Acad. Sci. USA 87: 4256-4260, Jun. 1990.
Alt et al., "Immunoglobulin genes in transgenic mice," Trends in Genetics 1: 231-236, Aug. 1985.
Baer et al., "Immunoglobulin V.sub.H genes are transcribed by T cells in association with a new 5' exon," J. Exp. Med. 167: 2011-2016, Jun. 1988.
Barbas et al., "Human Autoantibody Recognition of DNA," Proc. Natl. Acad. Sci. USA 92:2529-2533, Mar. 1995.

(Continued)

Primary Examiner — Anne Marie S Wehbe
(74) Attorney, Agent, or Firm — Baker Botts, L.L.P.

(57) ABSTRACT

The invention provides transgene constructs for expressing chimeric antibodies, and transgenic non-human host animals carrying such constructs, wherein the chimeric antibodies comprise human variable regions and constant regions of the non-human transgenic host animal. The presence of immunoglobulin constant regions of the host animal allows for generation of improved antibodies in such transgenic host animals. Subsequently, the chimeric antibodies can be readily converted to fully human antibodies using recombinant DNA techniques. Thus, the invention provides compositions and methods for generating human antibodies in which chimeric antibodies raised in vivo in transgenic mice are used as intermediates and then converted to fully human antibodies in vitro.

5 Claims, 1 Drawing Sheet

FOREIGN PATENT DOCUMENTS

| | | |
|---|---|---|
| EP | 0 592 106 | 4/1994 |
| EP | 0 814 159 | 12/1997 |
| GB | 2113715 | 8/1983 |
| WO | WO 90/04036 | 4/1990 |
| WO | WO 90/12878 | 11/1990 |
| WO | WO 91/00906 | 1/1991 |
| WO | WO 91/10741 | 7/1991 |
| WO | WO 92/01047 | 1/1992 |
| WO | WO 92/03917 | 3/1992 |
| WO | WO 92/03918 | 3/1992 |
| WO | WO 92/08474 | 5/1992 |
| WO | WO 93/11794 | 6/1993 |
| WO | WO 93/12227 | 6/1993 |
| WO | WO 94/25585 | 11/1994 |
| WO | WO 96/02576 | 2/1996 |
| WO | WO 96/02647 | 2/1996 |
| WO | WO 96/33735 | 10/1996 |
| WO | WO 96/34096 | 10/1996 |
| WO | WO 97/13852 | 4/1997 |
| WO | WO 98/24884 | 6/1998 |
| WO | WO 98/24893 | 6/1998 |
| WO | WO 99/45962 | 9/1999 |
| WO | WO 01/14424 | 3/2001 |
| WO | WO 01/25492 | 4/2001 |
| WO | WO 02/43478 | 6/2002 |

OTHER PUBLICATIONS

Berman et al., "Content and organization of the human Ig V.sub.H locus: definition of three new V.sub.H families and linkage to the Ig C.sub.H locus", EMBO Journal 7(3):727-738, 1988.

Berton et al., "Synthesis of germ-line .gamma.1 immunoglobulin heavy-chain transcripts in resting B cells: Induction by interleukin 4 and inhibition by interferon .gamma.", Proc. Natl. Acad. Sci. 86: 2829-2833, Apr. 1989.

Boer et al., "Polymorphisms in the Coding and Noncoding Regions of Murine Pgk-1 Alleles," Biochem. Genet. 28(5/6): 299-308, 1990.

Bollag et al., "Homologous recombination in mammalian cells," Ann. Rev. Genet. 23: 199-225, 1989.

Bosma et al., "A severe combined immunodeficiency mutation in the mouse," Nature 301: 527-530, Feb. 10, 1983.

Brownstein et al., "Isolation of Single-Copy Human Genes from a Library of Yeast Artificial Chromosome Clones," Science 244:1348-1351, Jun. 1989.

Bruggemann et al., "A repertoire of monoclonal antibodies with human heavy chains from transgenic mice," Proc. Natl. Acad. Sci. USA 86: 6709-6713, Sep. 1989.

Bruggemann et al., "Human antibody production in transgenic mice: expression from 100 kb of the human IgH locus," European Journal of Immunology 21:1323-1326, May 1991.

Bruggemann et al., "Strategies for expressing human antibody repertoires in trasgenic mice," Immunology Today, 17(8): 391-397, Aug. 1996.

Bucchini et al., "Rearrangement of a chicken immunoglobulin gene occurs in the lymphoid lineage of transgenic mice," Nature 326: 409-411, 1987.

Burke et al., "Cloning of Large Segments of Exogenous DNA into Yeast by Means of Artificial Chromosome Vectors," Science 236:806-812, May 1987.

Buttin, "Exogenous Ig gene rearrangement in transgenic mice: a new strategy for human monoclonal antibody production?" Trends in Genetics 3(8): 205-207, Aug. 1987.

Bye et al., "Germline Variable Region Gene Segment Derivation of Human Monoclonal Anti-Rh (D) Antibodies; Evidence for Affinity Maturation by Somatic Hypermutation and Repertoire Shift," J. Clin. Invest. 90(6): 2481-2490, Dec. 1992.

Campbell et al., "Totipotency or Multipotentiality of cultured cells: Applications and Progress," Theriogenology 47(1): 63-72, 1997.

Capecchi, "Altering the genome by homologous recombination," Science 244: 1288-1292, 1989.

Capecchi, "The new mouse genetics: Altering the genome by gene targeting," Trends In Genetics 5(3) :70-76, Mar. 1989.

Casali et al., "Frequency of B Cells Committed to the Production of Antibodies to Insulin in Newly Diagnosed Patients with Insulin-Dependent Diabetes Mellitus and Generation of High Affinity Human Monoclonal IgG to Insulin," J. Immunol. 144(10): 3741-3747, May 15, 1990.

Casali et al., "High-Affinity Antibodies to ssDNA are Produced by CD.sup.- B Cells in Systemic Lupus Erythematosus Patients," J. Immunol. 143(11): 3476-3483, Dec. 1, 1989.

Cha et al., "Combinatorial Autoantibodies to Dihydrolipoamide Acetyltransferase, the Major Autoantigen of Primary Biliary Cirrhosis," Proc. Natl. Acad. Sci. USA 90: 2527-2531, Mar. 1993.

Cha et al., "Heterogeneity of Combinatorial Human Autoantibodies Against PDC-E2 and Biliary Epithelial Cells in Patients with Primary Biliary Cirrhosis," Hepatol. 20(3): 574-583, 1994.

Chen et al., "B cell development in mice that lack one or both immunoglobulin .chi. light chain genes," EMBO J., 12(3): 821-830, 1993.

Chen et al., "Characterization of Two Immunoglobulin V.sub.H Genes that are Homologous to Human Rheumatoid Factors," Arthritis Rheum. 32(1): 72-76, Jan. 1989.

Chen et al., "Immunoglobulin gene rearrangement in B cell deficient mice generated by targeted deletion of the J.sub.H locus," Int. Immun. 5: 647-656, 1993.

Chen et al., "Mutations of the intronic IgH enhancer and its flanking sequences differentially affect accessibility of the J.sub.H locus," EMBO J. 12(12): 4635-4645, 1993.

Ch'ng et al., "Antisense RNA complementary 3' coding and noncoding sequences of creatine kinase is a potent inhibitor of translation in vivo," Prod. Natl. Acad. Sci. USA 86: 10006-10010, Dec. 1989.

Choi et al., "RNA splicing generates a variant light chain from an aberrantly rearranged .kappa. gene," Nature 286: 776-779, Aug. 21, 1980.

Choi et al., "Transgenic mice containing a human heavy chain immunoglobulin gene fragment cloned in a yeast artificial chromosome," Nature Genetics 4: 117-123, Jun. 1993.

Clackson et al., "Making antibody fragments using phage display libraries," Nature 352: 624-628, Aug. 15, 1991.

Co and Queen, "Humanized antibodies for therapy," Nature 351: 501-502, Jun. 6, 1991.

Coffman et al., "T cell activity that enhances polyclonal IgE production and its inhibition by interferon.gamma.," J. Immunol. 136: 949-954, 1986.

Coffman et al., A mouse T cell product that preferentially enhances IgA production, J. Immunol. 139: 3685-3690, 1987.

Davies et al., "Creation of Mice Expressing Human Antibody Light Chains by Introduction of a Yeast Artificial Chromosome Containing the Core Region of the Human Immunoglobulin .kappa. Locus," Biotechnology 11: 911-914, Aug. 11, 1993.

Davies et al., "Target alterations in yeast artificial chromosomes for inter-species gene transfer," Nucleic Acids Research 20(11): 2693-2698, 1992.

Ditzel et al., "The nature of autoimmune antibody repertoire in human immunodeficiency virus type 1 infection," Proc. Natl. Acad. Sci. USA 91: 3710-3714, Apr. 1994.

Doetschman et al., "Targetted correction of a mutant HPRT gene in mouse embryonic stem cells," Nature 330: 576-578, Dec. 1987.

Durdik et al., "Isotype switching by a microinjected .mu. immunoglobulin heavy chain gene in transgenic mice," Proc. Natl. Acad. Sci. USA 86: 2346-2350, 1989.

Ehrenstein et al., "Production of Human Monoclonal Antibodies to Myeloperoxidase," Immunol. 76: 617-620, 1992.

Eliceiri et al., "Stable integration and expression in mouse cells of yeast artificial chromosomes harboring human genes," Proc. Natl. Acad. Sci. 88: 2179-2183, Mar. 1991.

Esser and Radbruch, "Rapid induction of transcription of unrearranged S.gamma.1 switch regions in activated murine B cells by interleukin 4," EMBO Journal 8: 483-488, 1989.

Ferrier et al., "Separate elements control DJ and VDJ rearrangement in a transgenic recombination substrate," EMBO Journal 9(1): 117-125, Jan. 1990.

Fishwild et al., "High-avidity human IgG.kappa. monoclonal antibodies from a novel strain of minilocus transgenic mice," Nature Biotechnology 14: 845-851, Jul. 1996.

Forni, "Extensive splenic B cell activation in IgM-transgenic mice," Eur. J. Immunol. 20: 983-989, 1990.

Garza et al., "Mapping the *Drosophila* Genome with Yeast Artificial Chromosomes," Science 246: 641-646, Nov. 3, 1989.
Gerstein et al., "Isotype switching of an immunoglobulin heavy chain transgene occurs by DNA recombination between different chromosomes," Cell 63: 537-548, Nov. 1990.
Gnirke et al., "Cloning and in vivo expression of the human GART gene using yeast artificial chromosomes," EMBO J. 10(7): 1629-1634, 1991.
Goldstein et al., "A Randomized Clinical Trial of OKT3 Monoclonal Antibody for Acute Rejection of Cadaveric Renal Transplants," New Engl. J. Med 313(6): 337-342, Aug. 8, 1985.
Goodhardt et al., "Rearrangement and expression of rabbit immunoglobulin .kappa. light chain gene in transgenic mice," Proc. Nat. Acad. Sci. USA 84:4229-4233, Jun. 1987.
Gordon, "Transgenic mice in immunology," The Mount Sinai Journal of Medicine 53(3): 223-231, Mar. 1986.
Gorick et al., "Three Epitopes on the Human Rh Antigen D Recognized by .sup.125I-Labeled Human Monoclonal IgG Antibodies," Vox Sang 55: 165-170, 1988.
Green et al., "Antigen-specific human monoclonal antibodies from mice engineered with human Ig heavy and light chains YACs," Nature Genetics 7: 13-21, May 1994.
Hagman et al., "Inhibition of immunoglobulin gene rearrangement by the expression of a .lamda.2 transgene," J. Exp. Med. 169: 1911-1929, Jun. 1989.
Han et al., "Inhibition of Moloney murine leukemia virus-induced leukemia in transgenic mice expressing antisense RNA complementary to the retroviral packaging sequences," Proc. Natl. Acad. Sci. USA 88(10): 4313-4317, May 1991.
Hansen et al., "Interleukin-6 Autoantibodies: Possible Biological and Clinical Significance," Leukemia 9: 1113-1115, 1995.
Harding and Lonberg, "Class switching in human immunoglobulin transgenic mice," Annals of NY Acad. Sci., 764: 536-546, 1995.
Hasty et al., "Introduction of a subtle mutation into the Hox-2.6 locus in embryonic stem cells," Nature 350: 243-246, Mar. 21, 1991.
Hayakawa et al., Immunoglobulin-bearing B cells reconstitute and maintain the murine Ly-1 B cell lineage, Eur. J. Immun. 16: 1313-1316, 1986.
Helene et al., "Specific regulation of gene expression by antisense, sense and antigene nucleic acids," Biochimica et Biophysica Acta 1049: 99-125, 1990.
Hofker et al., "Complete physical map of the human immunoglobulin heavy chain constant region gene complex," Proc. Natl. Acad. Sci. USA 86: 5567-5571, Jul. 1989.
Humphries et al, "A new human immunoglobulin V.sub.H family preferentially rearranged in immature B-cell tumours," Nature 331: 446-449, Feb. 1988.
Huse et al., "Generation of a Large Combinatorial Library of the Immunoglobulin Repertoire in Phage Lambda," Science 246: 1275-1281, Dec. 8, 1989.
Huxley et al., "The Human HPRT Gene on a Yeast Artificial Chromosome is Functional when Transferred to Mouse Cells by Cell Fusion," Genomics 9:742-750, 1991.
Ichihara et al., "Organization of human immunoglobulin heavy chain diversity gene loci," EMBO Journal 7(13): 4141-4150, 1988.
Ichiyoshi et al., "A Human Anti-Insulin IgG Autoantibody Apparently Arises Through Clonal Selection from an Insulin-Specific 'Germ-Line' Natural Antibody Template," J. Immunol. 154: 226-238, 1995.
Iglesias et al., "Expression of immunoglobulin delta chain causes allelic exclusion in transgenic mice," Nature 330: 482-484, Dec. 1987.
Isaacs et al., "Humanised Monoclonal Antibody Therapy for Rheumatoid Arthritis," The Lancet 340: 748-752, Sep. 26, 1992.
Jaenisch, "Transgenic Animals," Science 240: 1468-1474, Jun. 1988.
Jakobovits et al., "Analysis of homozygous mutant chimeric mice: Deletion of the immunoglobulin heavy-chain joining region blocks B-cell development and antibody production," Proc. Natl. Acad. Sci. USA 90: 2551-2555, Mar. 1993.
Jakobovits et al., "Germ-line transmission and expression of a human-derived yeast artificial chromosome," Nature 362: 255-258, Mar. 18, 1993.

Jakobovits et al., "Production of Antigen-Specific Human Antibodies from Mice Engineered with Human Heavy and Light Chain YACs," Annals of the New York Academy of Sciences, NY Academy of Sciences, NY, USA, 764:525-535, Sep. 29, 1995.
Jakobovits, "Humanizing the mouse genome," Curr. Biol. 4(8): 761-763, 1994.
Jakobovits, "Production of fully human antibodies by transgenic mice," Curr. Opin. Biotechnol. 6(5): 561-566, 1995.
James and Bell, "Human monoclonal antibody production: current status and future prospects," J. Immunol. Methods 100: 5-40, 1987.
Janeway et al., Immunobiology, 3rd Edition, Garland Publishing, NY, US, 3:13 and 3:21, 1997.
Jasin and Berg, "Homologous integration in mammalian cells without target gene selection," Genes & Development 2: 1353-1363, 1988.
Ji et al., "Flow cytometry analysis of the neuralization effect of anti-ILB monoclonal antibodies on IL-8 activated human granulocytes," Shi Yan Sheng Wu Xue Bao 28(3): 257-261, Sep. 1995.
Johnson et al., "Targeting of nonexpressed genes in embryonic stem cells via homologous recombination," Science 245:1234-1236, Sep. 15, 1989.
Jonker et al., "In vivo Treatment with a Monoclonal Chimeric Anti-CD4 Antibody Results in Prolonged Depletion of Circulating CD4.sup.+ Cells in Chimpanzees," Clin. Exp. Immunol. 93: 301-307, 1993.
Judde et al, "Characterization of the Human Immunoglobulin Kappa Gene 3' Enhancer: Functional Importance of Three Motifs that Demonstrate B-Cell-Specific in vivo Footprints," Molecular and Cellular Biology, 12(11): 5206-5216, Nov. 1992.
Jung et al., "Shutdown of class switching recombination by deletion of a switch region control element," Science 259: 984-987, Feb. 1993.
Kasaian et al., "Identification and Analysis of a Novel Human Surface CD5- B Lymphocyte Subset Producing Natural Antibodies," J. Immunol. 148(9): 2690-2702, May 1, 1992.
Kelley et al., "Nonproductive kappa immunoglobulin genes: recombinational abnormalities and other lesions affecting transcription, RNA processing, turnover, and translation," Mol. Cell Bio. 5(7): 1660-1675, Jul. 1985.
Kenny et al., "Alteration of the B cell surface phenotype, immune response to phosphocholine and the B cell repertoire in M167 .alpha. plus .kappa. trsnsgenic mice," J. of Immunol. 142(12): 4466-4474, Jun. 1989.
Kitamura et al., "A B cell-deficient mouse by targeted disruption of the membrane exon of the immunoglobulin .mu. chain gene," Nature 350: 423-426, Apr. 1991.
Knox et al., "Observations on the effect of chimeric anti-CD4 monoclonal antibody in patients with Mycosis Fungoids," Blood 77(1): 20, Jan. 1991.
Kohler and Milstein, "Continuous cultures of fused cells secreting antibody of predefined specificity," Nature 256: 495-497, Aug. 7, 1975.
Kohler and Milstein, "Derivation of specific antibody-producing tissue culture and tumor lines by cell fusion," Eur. J. Immunol. 6: 511-519, 1976.
Koller and Smithies, "Inactivating the .beta..sub.2-microglobulin locus in mouse embryonic stem cells by homologous recombination," Proc. Natl. Acad. Sci. USA 86: 8932-8935, Nov. 1989.
Kurdowska et al., "An anti-interleukin 8 monoclonal antibody that interferes with the binding of interleukin 8 to cellular receptors and the activation of human blood neutrophils," Hybridoma 14(3): 225-233, 1995.
Laird et al., "Simplified mammalian DNA isolation procedure," Nucl. Acids Res. 19(15): 4293, 1991.
Lanzavecchia, "Antigen-specific interaction between T and B cells," Nature 314: 537-539, Apr. 11, 1985.
Larrick et al., "Generation of specific human monoclonal antibodies by in vitro expansion of human B cells: a novel recombinant DNA approach," In Vitro Immunization in Hybridoma Technology, Elsevier Science Publishers, Amsterdam, 231-246, Feb. 1988.
Larrick et al., "Rapid cloning of rearranged immunoglobulin genes from human hybridoma cells using mixed primers and the polymerase chain reaction," Biochem. Biophys. Res. Comm. 160(3): 1250-1256, May 15, 1989.

Lin et al., "Recombination in mouse L cells between DNA introduced into cells and homologous chromosomal sequences," Proc. Natl. Acad. Sci. USA 82: 1391-1395, Mar. 1985.

Linton et al., "Primary antibody-forming cells secondary B cells are generated from separate precursor cell subpopulations," Cell 59: 1049-1059, 1989.

Lo et al., "Expression of mouse IgA by transgenic mice, pigs and sheep," Eur. J. Immunol. 21: 1001-1006, 1991.

Lonberg et al., "A transgenic mouse that expresses a diversity of human sequence heavy and light chain immunoglobulins," Journal of Cellular Biochemistry Supplement 17(B): 204, 1993.

Lonberg et al., "Antigen-specific human antibodies from mice comprising four distinct genetic modifications," Nature 368: 856-859, Apr. 1994.

Lonberg et al., "Human Antibodies from Transgenic Mice," International Reviews of Immunology, Harwood Academic Publishers, London, 13:65-93, 1995.

Lonberg et al., "Human sequence antibodies from transgenic mice," J. of Cellular Biochemistry Supplement 18D: 185, 1994.

Lorenz et al., "Physical map of the human immunoglobulin .kappa. locus and its implications for mechanisms of V.sub..kappa. -J.sub..kappa. rearrangement," Nucleic Acids Research 15(23): 9667-9676, 1987.

Lutzker and Alt, "Structure and expression of germ line immunoglobulin .gamma.2b transcripts," Mol. Cell Biol. 8(4): 1849-1852, Apr. 1988.

Mansour et al., "Disruption of the proto-onogene int-2 in mouse embryo-derived stem cells: a general strategy for targeting mutations to non-selectable genes," Nature 336: 348-352, Nov. 1988.

Manz et al., "Feedback inhibition of immunoglobulin gene rearrangment by membrane mu, but not by secreted mu heavy chains," J. Exp. Med. 168: 1363-1381, Oct. 1988.

Marcu et al., "5' Flanking region of immunoglobulin heavy chain constant region genes displays length heterogeneity in germlines of inbred mouse strains," Cell 22: 187-196, Nov. 1980.

Marks et al., "By-passing immunization: Human antibodies from V-gene libraries displayed on phage," J. Mol. Biol. 222: 581-597, 1991.

Marsh et al., "The pIC plasmid and phage vectors with versatile cloning sites for recombinant selection by insertional inactivation," Gene 32: 481-485, 1984.

Marx, "Learning how to bottle the immune system," Science 246: 1250-1251, Dec. 8, 1989.

Matsuda et al., "Structure and physical map of 64 variable segments in the 3' 0.8-megabase region of the human immunoglobulin heavy-chain locus," Nature Genetics 3: 88-94, Jan. 1993.

Max et al., "Sequences of five potential recombination sites encoded close to an immunoglobulin .kappa. constant region gene," PNAS 76(7): 3450-3454, Jul. 1979.

McCormick et al., "Construction of human chromosome 21-specific yeast artifical chromosomes," Proc. Natl. Acad. Sci. USA 86: 9991-9995, Dec. 1989.

McMahon and Bradley, "The Wnt-1 (int-1) proto-onocogene is required for development of a large region of the mouse brain," Cell 62: 1073-1085, Sep. 21, 1990.

Melchers et al., "Cellular stages and molecular steps of murine B-cell development", Cold Spring Harbor Symposia on Quantitative Biology, vol. LIV, Cold Spring Harbor Lab Press, pp. 183-189, 1989.

Meyer and Neuberger, "The immunoglobulin .chi. locus contains a second, stronger B-cell-specific enhancer which is located downstream of the constant region," EMBO J. 8(7): 1959-1964, 1989.

Miller et al., "Structural alterations in J regions of mouse immunoglobulin .gamma. genes are associated with differential gene expression," Nature 295: 428-430, Feb. 1982.

Mills et al., "DNase I hypersentitive sites in the chromatin of human .mu. immunoglobulin heavy-chain genes," Nature 306: 809-812, 1983.

Mills et al., "Sequences of human immunoglobulin switch regions: implications for recombination and transcription," Nucl. Acids Res. 18:7305-7316, 1991.

Molecular Basis of Cancer Therapy, (Keystone Symposia, CO, Mar. 4-10, 1994) J. Cellular Biochem., Suppl. 18D: 97-116, 1994.

Mombaerts et al., "Creation of a large genomic deletion at the T-cell antigen receptor .beta.-subunit locus in mouse embryonic stem cells by gene targeting," Proc. Natl. Acad. Sci. USA 88: 3084-3087, Apr. 1991.

Mombaerts et al., "RAG-1-deficient mice have no mature B and T lymphocytes," Cell 68: 869-877, Mar. 6, 1992.

Morel et al., "Down-Regulation of Lymphocyte CD4 Antigen Expression by Administration of Anti-CD4 Monoclonal Antibody," Clin. Immuno. Immunopath. 64(3): 248-253, Sep. 1992.

Morrison, "Success in specification," Nature 368: 812-813, Apr. 1994.

Mowatt et al., "DNA sequence of the murine .gamma.1 switch segment reveals novel structural elements," J. Immunol. 136(7): 2674-2683, Apr. 1986.

Mudgett-Hunter et al., "Binding and structural diversity among high-affinity monoclonal anti-digoxin antibodies," Molecular Immunology 22(4): 477-488, Apr. 1985.

Muller et al., "Membrane-bound IgM obstructs B cell development in transgenic mice," Eur. J. Immunol. 19: 923-928, 1989.

Munir et al., "Antisense RNA Production in Transgenic Mice," Somatic Cell and Molecular Genetics 16(4): 383-394, 1990.

Murray and Szostak, "Construction of artificial chromosomes in yeast," Nature 305: 189-193, Sep. 1983.

Nakamura et al., "Probing the Normal and Autoimmune B Cell Repertoire with Epstein-Barr Virus, Frequency of B Cells Producing Monoreactive High Affinity Autoantibodies in Patients with Hashimoto's Disease and Systemic Lupus Erythematosus," J. Immunol. 141(12): 4165-4172, Dec. 15, 1988.

Neuberger et al., "Isotype exclusion and transgene down-regulation in immunoglobulin-.lamda. transgenic mice," Nature 338: 350-352, Mar. 1989.

Neuberger, "Generating high-avidity human Mabs in mice," Nature Biotechnology 14: 826, Jul. 1996.

Newkirk et al., "Complete protein sequences of the variable regions of the cloned heavy light chains of a human anti-cytomegalovirus antibody reveal a striking similarity to human monoclonal rheumatoid factors of the Wa idiotypic family," J. Clin. Invest. 81: 1511-1518, May 1988.

Newman et al., "'Primatization' of recombinant antibodies for immunotherapy of human diseases: a Macaque/human chimeric antibody against human C4," Biotechnology 10(11): 1455-1460, Nov. 1992.

Nikaido et al., "Nucleotide sequences of switch regions of immunoglobulin C.sub..epsilon. and C.sub..gamma. genes and their comparison," J. Biol. Chem. 257(13): 7322-7329, Jul. 1982.

Nikaido et al., "Switch region of immunglobulin C.mu. gene is composed of simple tandem repetitive sequences," Nature 292: 845-848, Aug. 1981.

Nussenzweig et al., "A human immunoglobulin gene reduces the incidence of lymphomas in c-Myc-bearing transgenic mice," Nature 336: 446-450, Dec. 1988.

Nussenzweig et al., "Allelic exclusion in transgenic mice carrying mutant human IgM genes," J. Exp. Med. 167: 1969-1974, Jun. 1988.

O'Conner et al., "Construction of large DNA segments in E. coli,"Science 244: 1307-1312, Jun. 16, 1989.

Oettinger et al., "RAG-1 and RAG-2, Adjacent genes that synergistically activate V(D)J Recombination," Science 248: 1517-1523, 1990.

Ogino et al., "Affinity Studies of Human Anti-MAG Antibodies in Neuropathy," J. Neuroimmunol. 52: 41-46, 1994.

Orkin et al., "Mutation in an intervening sequence splice junction in man," Proc. Natl. Acad. Sci. USA 78(8): 5041-5045, Aug. 1981.

Orlandi et al., "Cloning imunoglobulin variable domains for expression by the polymerase chain reaction," Proc. Natl. Acad. Sci. USA 86: 3833-3837, 1989.

Ostberg and Pursch, "Human x (Mouse x Human) Hybridomas Stably Producing Human Antibodies," Hybridoma, 2(4): 361-367, 1983.

Ott and Marcu, "Molecular requirements for immunoglobulin heavy chain constant region gene switch-recombination revealed with switch-substrate retroviruses," Intl. Immunol., 1(6):582-591, 1989.

Ott et al., "Immunoglobulin heavy chain switch region recombination within a retrovrial vector in murine pre-B cells," EMBO Journal 6(3):577-587, 1987.

Pachnis et al., "Transfer of a yeast artificial chromosome carrying human DNA from *Saccharomyces cerevisae* into mammalian cells," Proc. Natl. Acad. Sci. USA 87: 5109-5113, Jul. 1990.

Pascual et al., "The complete nucleotide sequences of the heavy chain variable regions of six monospecific rheumatoid factors derived from Epstein-Barr virus-transformed B cells isolated from the synovial tissue of patients with rheumatoid arthritis," J. Clin. Invest. 86: 1320-1328, Oct. 1990.

Pavan et al., "Modification and Transfer into an Embryonal Carcinoma Cell Line of a 360-Kilobase Human-Derived Yeast Artificial Chromosome," Mol. Cell Biol. 10(8): 4163-4169, Aug. 1990.

Pedersen and Andreasen, "An Approach for Characterization and Purification of a Human Monoclonal Hybridoma Antibody," Hybridoma 8(1): 97-105, 1989.

Perera et al., "Isolation and characterization of monoclonal antibodies to Shiga-like toxin II of enterohemorrhagic *Escherichia coli* and use of the monoclonal antibodies in a colony enzyme-linked immunosorbent assay," J. Clin. Microbiology 26(10): 2127-2131, Oct. 1988.

Petersen et al., "A Human-Mouse Hybridoma which Secretes Monoclonal Thyroglobulin Autoantibody with Properties Simliar to Those of the Donor Patient's Serum Autoantibody," Autoimmunity 4: 89-102, 1989.

Petters, "Transgenic mice in immunological research," Vet. Immunol. Immunopath 17: 267-278, 1987.

Pettersson, et al., "A second B cell-specific enhancer 3' of the immunoglobulin heavy-chain locus," Nature 344: 165-168, Mar. 1990.

Pieper et al., "Efficient generation of functional transgenes by homologous recombination in murine zygotes," Nucleic Acids Res. 20(6): 1259-1264, 1992.

Powelson et al., "CDR-Grafted OKT4A Monoclonal Antibody in Cynomolgus Rena Allograft Recipients," Transplantation 57(6): 788-793, Mar. 1994.

Rabbits et al., "Human immunoglobulin heavy chain genes: evolutionary comparisons of C.mu., C.delta. C.gamma. genes and associated switch sequences," Nucl. Acids Res. 9: 4509-4524, 1981.

Rapoport et al., "Combinatorial Libraries: New Insights into Human Organ-Specific Autoantibodies," Immunol. Today 16(1): 43-49, 1995.

Rath et al., "B cell abnormalities induced by a .mu. Ig transgene extend to L chain isotype usage," J. of Immunol. 146(8): 2841-2847, Apr. 1991.

Rath et al., "Quantitative analysis of idiotypic mimicry and allelic exclusion in mice of a .mu. Ig transgene," J. of Immunol., 143(6): 2074-2080, Sep. 1989.

Ravetch et al., "Evolutionary approach to the question of immunoglobulin heavy chain switching: Evidence from cloned human mouse genes," Proc. Natl. Acad. Sci. 77: 6734-6738, 1980.

Reid et al., "A single DNA response element can confer inducibility by both .alpha.- and .gamma.- interferons," Proc. Natl. Acad. Sci. USA 86: 840-844, 1989.

Richter et al., "Immunoglobulin Variable Gene Analysis of Human Autoantibodies Reveals Antigen-driven Immune Response to Glutamate Decarboxylase in Type 1 Diabetes Mellitus," Eur. J. Immunol. 25: 1703-1712, 1995.

Ritchie et al., "Allelic exclusion and control of endogenous immunoglobulin gene rearrangement in .kappa. transgenic mice," Nature 312:512-520, Dec. 1984.

Rothman et al., "Structure and expression of germline immunoglobulin .gamma.3 heavy chain gene transcripts: implications for mitogen and lymphokine directed class-switching," Intl. Immunol. 2: 621-627, 1990.

Rusconi et al., "Transmission and expression of a specific pair of rearranged immunoglobulin .mu. and .kappa. genes in a transgenic mouse line," Nature 314: 330-334, Mar. 28, 1985.

Sakano et al., "Sequences at the somatic recombination sites of immunoglobulin light-chain genes," Nature 280:288-294, Jul. 26, 1979.

Sakano et al., "Two types of somatic recombination are necessary for the generation of complete immunoglobulin heavy-chain genes," Nature 286:676-683, Aug. 14, 1980.

Sanchez et al., "Compartmentalization of .lamda. subtype expression in the B cell repertoire of mice with a disrupted or normal C.sub.78 gene segment," Intl. Immunol. 6(5): 711-719, 1994.

Sasano et al., "Molecular Selection of Human Antibodies With an Unconventional Bacterial B Cell Antigen," J. Immunol. 151(10): 5822-5839, Nov. 15, 1993.

Sastry et al., "Cloning of the immunological repertoire in *Escherichia coli* for generation of monoclonal catalytic antibodies: Construction of a heavy chain variable region-specfic cDNA library," Proc. Natl. Acad. Sci. USA 86: 5728-5732, Aug. 1989.

Sato et al., "Physical linkage of a variable region segment and the joining region segment of the human immunoglobulin heavy chain locus," Biochem. Biophys. Res. Comm. 154: 264-271, 1988.

Sawada et al., "Production and Characterization of Monoclonal and Polyclonal Antibodies against Digoxin," Bul. Natl. Inst. Hyg. Sci. 9108: 29-33, 1990.

Scangos and Bieberich, Gene transfer into mice, Advances in Genetics 24: 285-322, 1987.

Scwartzberg et al., "Germ-line transmission of c-abl mutation produced by targeted gene disruption in ES cells," Science 246:799-803, Nov. 10, 1989.

Sedivy and Sharp, "Positive genetic selection for gene disruption in mammalian cells by homologous recombination," Proc. Natl. Acad. Sci. USA 86: 227-231, 1989.

Seidman and Leder, "A mutant immunoglobuline light chain is formed by aberrant DNA- and RNA-splicing events," Nature 286:779-783, Aug. 21, 1980.

Sekido et al., "Prevention of lung reperfusion injury in rabbits by a monoclonal antibody against interleukin-8," Nature 356: 654-657, Oct. 14, 1993.

Serwe and Sablitzky, "V(D)J recombination in B cells is impaired but not blocked by targeted deletion of the immunoglobulin heavy chain intron enhancer," EMBO J. 12(6): 2321-2327, 1993.

Shen et al., "Human heavy-chain variable region gene family nonrandomly rearranged in familial chronic lymphocytic leukemia," Proc. Natl. Acad. Sci. USA 84: 8563-8567, Dec. 1987.

Shimizu et al., "Immunoglobulin double-isotype expression by trans-mRNA in a human immunoglobulin transgenic mouse," Proc. Natl. Acad. Sci. USA 86: 8020-8023, Oct. 1989.

Shimizu et al., "Trans-splicing as a possible molecular mechanism for the multiple isotype expression of the immunoglobulin gene," J. Exp. Med. 173: 1385-1393, Jun. 1991.

Shin et al., "Physical map of the 3' region of the human immunoglobulin heavy chain locus: clustering of autoantibody-related variable segments in one haplotype," EMBO Journal 10(12): 3641-3645, 1991.

Sideras et al., "Production of sterile transcripts of C.sub.65 genes in an IgM-producing human neoplastic B cell ine that switches to IgG-producing cells," Intl. Immunol. 1: 631-642, 1989.

Siebenlist et al., "Human immunoglobulin D segments encoded in tandem multigenic families," Nature 294: 631-635, Dec. 1981.

Silberstein et al., "Variable Region Gene Analysis of Pathologic Human Autoantibodies to the Related i and I Red Blood Cell Antigens," Blood 78(9): 2372-2386, Nov. 1, 1991.

Smithies et al., "Insertion of DNA sequences into the human chromosomal .beta.-globulin locus by homologous recombination," Nature 317: 230-234, Sep. 1985.

Snapper et al., "Interferon-.gamma. and B cell stimulatory factor-1 reciprocally regulate Ig isotype production," Science 236: 944-947, 1987.

Song et al., "Accurate modification of a chromosomal plasmid by homologous recombination in human cells," Proc. Natl. Acad. Sci. USA 84: 6820-6824, Oct. 1987.

Soriano et al., "Targeted disruption of the c-src proto-oncogene leads to osteopetrosis in mice," Cell 64: 693-702, Feb. 1991.

Spitzer et al., "Autoantibody to the Alternative Pathway C3/C5 Convertase and its Anti-Idiotypic Response," J. Immunol. 148(1): 137-141, Jan. 1, 1992.

Stavnezer et al., "Immunoglobulin heavy-chain switching may be directed by prior induction of transcripts from constant region genes," Proc. Natl. Acad. Sci. 85: 7704-7708, 1988.

Stites et al., Basic & Clinical Immunology, p. 50, 1984.

Storb et al., "Expression of a microinjected immunoglobulin kappa gene in transgenic mice," Banbury Reports 20: 197-207, 1985.

Storb et al., "Expression, allelic exclusion and somatic mutation of mouse immunoglobulin kappa genes," Immunol. Revs. 89: 85-102, 1986.

Storb, "Immunoglobulin gene analysis in transgenic mice," Immunoglobulin Genes, Academic Press Limited, pp. 303-326, 1989.

Stout and Caskey, "Antisense RNA Inhibition of HPRT Synthesis," Somatic Cell and Molecular Genetics 16(4): 369-382, 1990.

Szurek et al., "Complete nucleotide sequence of the murine .gamma.3 switch region and analysis of switch recombination in two .gamma.3-expressing hybridomas," J. Immunol. 135(1): 620-626, Jul. 1985.

Tahara et al., "HLA antibody responses in HLA class I transgenic mice," Immunogenetics 32: 351-360, 1990.

Takeda et al., "Deletion of the immunoglobulin kappa chain intron enhancer abolishes kappa chain gene rearrangement in cis but not lambda chain rearrangement in trans," EMBO J. 12(6): 2329-2336, 1993.

Taki et al., "Targeted insertion of a variable region gene into the immunoglobulin heavy chain locus," Science 262: 1268-1271, 1993.

Tanaka et al., "An antisense oligonucleotide complementary to a sequence in I.gamma.2b increases .gamma.2b germline transcripts, stimulates B cell DNA synthesis, and inhibits immunoglobulin secretion," J. Exp. Med. 175: 597-607, Feb. 1992.

Taussig et al., "Regulation of immunoglobulin gene rearrangment and expression," Immunology Today 10(5):143-146, 1989.

Taylor et al., "A Transgenic Mouse that Expresses a Diversity of Human Sequence Heavy and Light Chain Immunoglobulins," Nucleic Acids Research 20(23): 6287-6295, Dec. 11, 1992.

Taylor et al., "Human immunoglobulin transgenes undergo rearrangement, somatic mutation and class switching in mice that lack endogenous IgM," International Immunology 6(4): 579-591, 1994.

Thomas and Capechi, "Site-directed mutagenesis by gene targeting in mouse embro-derived stem cells," Cell 51: 503-512, 1987.

Thomas and Capecchi, "High frequency targeting of genes to specific sites in the mammalian genome," Cell 44: 419-428, Feb. 1986.

Thorpe and Bailey, "Demonstration of Autoreactivity by a Human Monoclonal IgG Anti-Rh D Antibody," Brit. J. Haematology 83: 311-318, 1993.

Tomlinson et al, "The Repertoire of Human Germline V.sub.H Sequences Reveals about Fifty Groups of V.sub.H Segments with Different Hypervariable Loops," J. Mol. Biol. 227: 776-798, 1992.

Traver et al., "Rapid screening of human genomic library in yeast artificial chromosomes for single-copy sequences," Proc. Natl. Acad. Sci. USA 86: 5898-5902, Aug. 1989.

Treisman et al., "Specific transcription and RNA splicing defects in five cloned .beta.-thalassaemia genes," Nature 302:591-596, Apr. 14, 1983.

Tuaillon et al., "Human immunoglobulin heavy-chain minilocus recombination in transgenic mice: Gene-segment use in .mu. and .gamma. transcripts," Proc. Natl. Acad. Sci. USA 90(8): 3720-3724, Apr. 1993.

Tybulewicz et al., "Neonatal lethality and lymphopenia in mice with a homozygous disruption of the cabl proto-oconogene," Cell 65: 1153-1163, Jun. 28, 1991.

Uhlmann and Peyman, "Antisense Oligonucleotides: A new therapeutic principle," Chem. Revs. 90(4): 544-584, 1990.

Velge-Roussel et al., "Analysis of Human CD4-Antibody Interaction Using the BIAcore System," J. Immunol. Meth. 183: 141-148, 1995.

Vlasov et al., "Arrest of immunoglobuline G mRNA translation in vitro with an alkylating antisense olgionucleotide derivative," Chem. Abs. 112: 229433X, p. 28, 1990.

Wagner et al., "Antibodies generated from human immunoglobulin miniloci in transgenic mice," Nucleic Acids Research 22(8): 1389-1393, 1994.

Waldmann, "Immune Receptors: Targets for Therapy of Leukemia/ Lymphoma, Autoimmune Diseases and for the Prevention of Allograft Rejection," Annu. Rev. Immunol. 10: 675-704, 1992.

Ward et al., "Binding activities of a repertoire of single immunoglobulin variable domains secreted from *Escherichia coli*," Nature 341: 544-546, Oct. 12, 1989.

Weaver et al., "A transgenic immunoglobulin mu gene prevents rearrangment of endogenous genes," Cell 42: 117-127, Aug. 1985.

Weiss, "Mice making human-like antibodies," The Washington Post, Apr. 28, 1994.

Wigley et al., "Site-specific transgene insertion: an approach," Reprod. Fertil. Dev. 6: 585-588, 1994.

Winter and Milstein, "Man-made antibodies," Nature 349: 293-299, Jan. 24, 1991.

Wofsy et al., "Reversal of advanced murine lupus in NZB/NZWF F.sub.1 mice by treatment with monoclonal antibody to L3T4," J. Immunol. 138(10): 3247-3253, May 1987.

Woolf et al., "The use of digoxin-specific Fab fragments for severe digitalis intoxication in children," New Engl. J. Med. 326(26): 1739-1744, Jun. 25, 1992.

Yamamura et al., "Cell-type-specific and regulated expression of a human .lamda.1 heavy-chain immunoglobulin gene in transgenic mice," Proc. Natl. Acad. Sci. USA 83: 2152-2156, Apr. 1986.

Yancopoulos and Alt, "Regulation of the assembly and expression of variable-region genes," Ann. Rev. Immunol. 4: 339-368, 1986.

Yancopoulous and Alt,"Developmentally controlled and tissue-specific expression of unrearranged V.sub.H gene segments," Cell 40: 271-281, 1985.

Yasui et al., "Class switch from .mu. .delta. is mediated by homologous recombination between .sigma..sub..mu. and .SIGMA..sub.. mu. sequences in human immunoglobulin gene loci," Eur. J. Immunol. 19: 1399-1403, 1989.

Zachau, "Immunoglobulin Light-Chain Genes of the K Type in Man and Mouse," in Immunogloblulin Genes, Honjo et al. (eds.), Academic Press, London, 91-109, 1989.

Zimmer and Gruss, "Production of chimeric mice containing embryonic stem (ES) cells carrying a homoeobox Hox. 1.1 allele mutated by homologus recombination," Nature 338: 150-153, Mar. 1989.

Zlijstra et al., "Germ line transmission of a disrupted .beta..sub.2 microglobulin gene produced by homologous recombination in embryonic stem cells," Nature 342: 435-438, Nov. 1989.

Zou et al., "Gene targeting in the Ig kappa locus: Efficient generation of lambda chain-expressing B cells, independent of gene rearrangements in Ig kappa," EMBO J. 12(3): 811-820, 1993.

Babcook JS, et al., "A novel strategy for generating monoclonal antibodies from single, isolated lymphocytes producing antibodies of defined specificities," Proc Natl Acad Sci U S A. Jul. 23, 1996:7843-8.

Harmer IJ, et al., "Chimaeric monoclonal antibodies encoded by the human VH26 gene from naïve transgenic mice display a wide range of antigen-binding specificities," Immunology. Jun. 1996;88(2):174-82.

Mageed RA et al., "Rearrangement of the human heavy chain variable region gene V3-23 in transgenic mice generates antibodies reactive with a range of antigens on the basis of VHCDR3 and residues intrinsic to the heavy chain variable region," Clin Exp Immunol. Jan. 2001;123(1):1-8.

Tomizuka K et al., "Double trans-chromosomic mice: maintenance of two individual human chromosome fragments containing Ig heavey and kappa loci and expression of fully human antibodies," Proc Natl Acad Sci U S A. Jan. 18, 2000;97(2):722-7.

Zhou J, et al., "The origin of a developmentally regulated Igh replicon is located near the border of regulatory domains for Igh replication and expression," Proc Natl Acad Sci U S A. Oct. 15, 2002;99(21):13693-8. Epub Oct. 7, 2002.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 1
ggccgcacgc gtgtcgactc                                           20

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
gccgagtcga cacgcgtgc                                            19

<210> SEQ ID NO 3
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 3
ggccgcattc gccggctaac ggcgcctata acgagttc                       38

<210> SEQ ID NO 4
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 4
ggccgaacgg cttataggcg ccgttagccg gcgaatgc                       38

<210> SEQ ID NO 5
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 5
tcgaggccgg catgataggc gccgtcgaca                                30

<210> SEQ ID NO 6
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 6
agcttgtcga cggcgcctat catgccggcc                                30

<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7
tcgactccgc ggtttaaact gg                                        22
```

```
<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
ggcgccagtt taaaccgcgg ag                                              22

<210> SEQ ID NO 9
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 9
gctggaaaga gaactgtcgg agtggg                                          26

<210> SEQ ID NO 10
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 10
ccaaagtccc tatcccatca tccaggg                                         27
```

TRANSGENIC ANIMALS EXPRESSING CHIMERIC ANTIBODIES FOR USE IN PREPARING HUMAN ANTIBODIES

CROSS-REFERENCE TO RELATED APPLICATIONS

This application is a national phase of International Application No. PCT/US07/008231, filed Mar. 30, 2007, which claims priority to U.S. provisional application Ser. No. 60/744,104 filed Mar. 31, 2006, the contents of which are hereby incorporated in their entirety.

Sequence Listing

The specification further incorporates by reference the Sequence Listing submitted herewith via EFS on Jan. 28, 2009. Pursuant to 37 C.F.R. §1.52(e)(5), the Sequence Listing text file, identified as 0773750721.txt, is 2,022 bytes and was created on Jan. 23, 2009. The Sequence Listing, electronically filed herewith, does not extend beyond the scope of the specification and thus does not contain new matter.

BACKGROUND OF THE INVENTION

Antibodies have proven to be effective therapeutic agents in humans for the treatment of a wide variety of disorders, including cancer, autoimmune diseases and infectious diseases. Although originally mouse monoclonal antibodies were tried as therapeutic agents, they generally proved to be unsuitable for use in humans due to the occurrence of a human anti-mouse antibody (HAMA) response. Rather, antibodies composed in part or entirely of human antibody amino acid sequences currently are the antibody agents of choice for use in humans. Of the numerous antibodies approved by the FDA for use in humans or currently in clinical trials, certain antibodies contain mouse variable regions linked to human constant regions and typically are referred to as chimeric antibodies. Others contain mouse CDRs within human framework and constant regions and typically are referred to as humanized antibodies. Still others are composed entirely of human-derived sequences (i.e., fully human variable and constant regions) and typically are referred to as human antibodies.

A number of approaches are known in the art for preparing human antibodies. In one type of approach, a library of human immunoglobulin sequences is screened on a display system (e.g., bacteriophage) with an antigen of interest to select antibody sequences having the desired antigenic specificity (see e.g., U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.). Since this approach is carried out in vitro, the human antibody sequences do not undergo affinity maturation or somatic mutation during the selection process, which may result in antibodies of lower affinity as compared to antibodies generated in vivo.

Thus, in another type of approach, mice whose genomes have been modified to contain human immunoglobulin sequences are used to raise antigen-specific antibodies by immunization with an antigen of interest. Such mice carry unrearranged human immunoglobulin genes (variable and constant regions) on transgenes and/or transchromosomes, which genes undergo apparently normal rearrangement and isotype switching in the mice. Moreover, somatic mutation occur during the maturation of the antibody response in these mice.

One example of such a mouse is the HuMAb Mouse® (Medarex, Inc.), which contains human immunoglobulin transgene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368 (6474): 856-859). Accordingly, the mice exhibit reduced expression of mouse IgM or κ and, in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93 and Harding, F. and Lonberg, N. (1995) *Ann. N.Y. Acad. Sci.* 764:536-546). The preparation and use of HuMab mice, and the genomic modifications carried by such mice, are further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845 851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 by Korman et al.

An alternative transgenic mouse system for expressing human immunoglobulin genes is referred to as the Xenomouse (Abgenix, Inc.) and is described in, for example, U.S. Pat. Nos. 5,939,598; 6,075,181; 6,114,598; 6,150,584 and 6,162,963 to Kucherlapati et al. Like the HuMAb Mouse® system, the Xenomouse system involves disruption of the endogenous mouse heavy and light chain genes and insertion into the genome of the mouse transgenes carrying unrearranged human heavy and light chain immunoglobulin loci that contain human variable and constant region sequences.

Other systems known in the art for expressing human immunoglobulin genes include the KM Mouse® system, described in detail in PCT Publication WO 02/43478 by Ishida et al., in which the mouse carries a human heavy chain transchromosome and a human light chain transgene, and the TC mouse system, described in Tomizuka et al. (2000) *Proc. Natl. Acad. Sci. USA* 97:722-727, in which the mouse carries both a human heavy chain transchromosome and a human light chain transchromosome. In each of these systems, the transgenes and/or transchromosomes carried by the mice comprise human immunoglobulin variable and constant region sequences.

U.S. Pat. No. 6,596,541 provides a prophetic example of a homologous recombinant mouse that expresses chimeric antibodies having human variable region sequences linked to mouse constant region sequences. In the example, the mouse heavy chain locus variable region (V-D-J segments) is precisely replaced with the human heavy chain V-D-J counterpart via a multi-step process. First, a large genomic fragment (greater than 20 kb) spanning the human immunoglobulin variable gene segments of interest is obtained and bacterial recombination is used to prepare a large targeting vector for use in eukaryotic cells (LTVEC) that includes homology arms totaling greater than 20 kb. The homology arms contain sequences from the endogenous mouse immunoglobulin locus. The LTVEC is then introduced into mouse embryonic stem cells. A cell in which homologous recombination has occurred between the LTVEC and the endogenous mouse immunoglobulin locus is identified using a quantitative assay to detect modification of allele (MOA) in the ES cells. No actual mice expressing chimeric antibodies, however, are described or characterized.

SUMMARY OF THE INVENTION

In this invention, transgenic animals expressing chimeric antibodies, comprising human variable regions and non-human constant regions, are described and characterized. In particular, the constant regions are those of the host animal (e.g., in mice, the constant regions are mice constant regions). The animals of the invention can be made using transgenic microinjection technology and do not require the use of homologous recombination technology and thus are easier to prepare and select than approaches using homologous recombination. Moreover, the expression of the human Ig variable regions linked to the host animal Ig constant regions in the transgenic animals of the invention is thought to allow for improved trafficking and development of B cells and antibodies in vivo such that improved antibodies can be obtained in these animals, as compared to transgenic animals that express human Ig variable regions linked to human Ig constant regions. Such improvements in the antibodies can include, for example, increased somatic mutations, improved association with endogenous mouse accessory proteins, and improved binding to mouse Fc receptors in vivo.

Moreover, the chimeric antibodies can readily be converted to fully human antibodies by isolation of the sequences encoding the human V regions and linkage of these sequences to human constant region sequences using standard recombinant DNA technology in vitro. Thus, the invention provides a means to obtain improved human antibodies, suitable for use in therapy, through the use of a chimeric antibody intermediate raised in vivo in transgenic animals.

In the animals of the invention, a transgene comprising unrearranged human immunoglobulin variable region sequences and at least one host animal constant region sequence (e.g., an IgM constant region) is prepared and inserted into the genome of the host animal (e.g., by pronuclear microinjection into a zygote of the host animal). When inserted into the genome of the host animal, the transgene construct undergoes rearrangement and expresses chimeric antibodies in the non-human host animal, the chimeric antibodies comprising a human variable region and a constant region of the non-human host animal. Moreover, as demonstrated herein, the inserted transgene is capable of undergoing trans-switching in the host animal with endogenous constant regions such that chimeric antibodies of different isotypes are obtained in the animals.

Accordingly, in one aspect, the invention pertains to a transgene construct comprising a plurality of unrearranged human immunoglobulin (Ig) variable region sequences operatively linked to at least one immunoglobulin (Ig) constant region sequence of a non-human host animal, wherein the transgene construct undergoes rearrangement in the non-human host animal and expresses chimeric antibodies in the non-human host animal. The chimeric antibodies comprise a human variable region and a constant region of the non-human host animal. In a preferred embodiment, the plurality of unrearranged human Ig variable region sequences are heavy chain variable region sequences. Alternatively, the plurality of unrearranged human Ig variable region sequences can be light chain variable region sequences.

In a preferred embodiment, the construct comprises heavy chain variable region sequences comprising V-D-J sequences. For example, the construct can comprise, in 5' to 3' direction, a plurality of human $V_H$ regions, a plurality of human D segments, a plurality of human $J_H$ segments, a J-µ enhancer from a non-human host animal, a µ switch region from a non-human host animal and a µ constant region from a non-human host animal. In one embodiment, the construct comprises four human $V_H$ regions, 15 human D segments and six human $J_H$ segments. A preferred transgene construct is a 9B2 transgene construct.

As demonstrated herein, transgene constructs comprising human heavy chain V-D-J sequences linked to a µ constant region of the non-human host animal are capable of undergoing trans-switching with an endogenous constant region of the non-human host animal when the transgene construct is integrated into the genome of the non-human host animal such that chimeric antibodies of more than one isotype can be raised in the host animal. In a particularly preferred embodiment, the invention provides a transgene construct which comprises, in 5' to 3' direction, a plurality of human $V_H$ regions, a plurality of human D segments, a plurality of human $J_H$ segments, a mouse J-µ enhancer, a mouse µ switch region and a mouse µ constant region, wherein the transgene construct, when integrated into a mouse genome, undergoes trans-switching with an endogenous mouse γ constant region such that chimeric antibodies comprising human V regions and mouse constant regions of IgM and IgG isotype are produced in the mouse.

Although the presence of the µ constant region in the transgene construct has been shown to be sufficient for trans-switching to occur, in certain embodiments it may be preferable to include more host animal constant regions in the transgene construct itself, such that both trans-switching and cis-switching can occur to generate antibodies of different isotypes. Thus, in certain embodiments, the transgene construct can include, for example, a γ constant region from the non-human host animal or an α constant region from the non-human host animal. Alternatively, the transgene construct can comprise all Ig constant regions of the non-human host animal (i.e., the transgene construct comprises the entire constant region of the non-human host animal).

In another aspect, the invention pertains to transgenes for expressing chimeric antibodies in which the unrearranged human Ig variable region sequences are human light chain variable region sequences, such as human kappa V-J sequences, linked to light chain constant region sequences from the non-human host animal. For example, in one embodiment, the construct comprises, in 5' to 3' direction, a plurality of human $V_\kappa$ regions, a plurality of human $J_\kappa$ segments, a J-κ enhancer from a non-human host animal and a $C_\kappa$ coding region from a non-human host animal.

Another aspect of the invention pertains to transgenic non-human host animals comprising one or more transgene constructs of the invention, wherein the animal expresses chimeric antibodies comprising human Ig variable regions and non-human host animal constant regions. Preferably, the transgene undergoes trans-switching and the animal expresses chimeric antibodies comprising human Ig variable regions and non-human host animal Ig constant regions of at least the IgM and IgG isotypes. Preferred non-human host animals are mice, although other animals suitable for transgenesis are also encompassed by the invention. Moreover, preferably the endogenous immunoglobulin loci are inactivated in the non-human host animal, for example by homologous recombination. In a preferred embodiment, an endogenous heavy chain locus of the transgenic host animal is inactivated by disruption of the $J_H$ region. In another preferred embodiment, an endogenous light chain locus of the transgenic host animal is inactivated by disruption of the $J_\kappa$ region.

Yet another aspect of the invention pertains to a method of making a chimeric antibody specific for an antigen of interest. The method comprises immunizing a transgenic non-human host animal of the invention, which comprises a transgene construct of the invention, with the antigen of interest and obtaining from the animal a chimeric antibody specific for the antigen of interest. For example, hybridomas expressing chimeric antibodies can be prepared from the immunized host animal using standard techniques. In a preferred embodiment, the method further comprises isolating from the animal nucleic acid encoding the chimeric antibody, replacing nucleic acid encoding the non-human host animal Ig constant region with nucleic acid encoding a human Ig constant region to thereby convert the chimeric antibody to a human antibody and expressing the human antibody. In certain embodiments, the human antibody exhibits higher affinity toward the antigen of interest than the chimeric antibody.

DETAILED DESCRIPTION OF THE INVENTION

Figure 1:
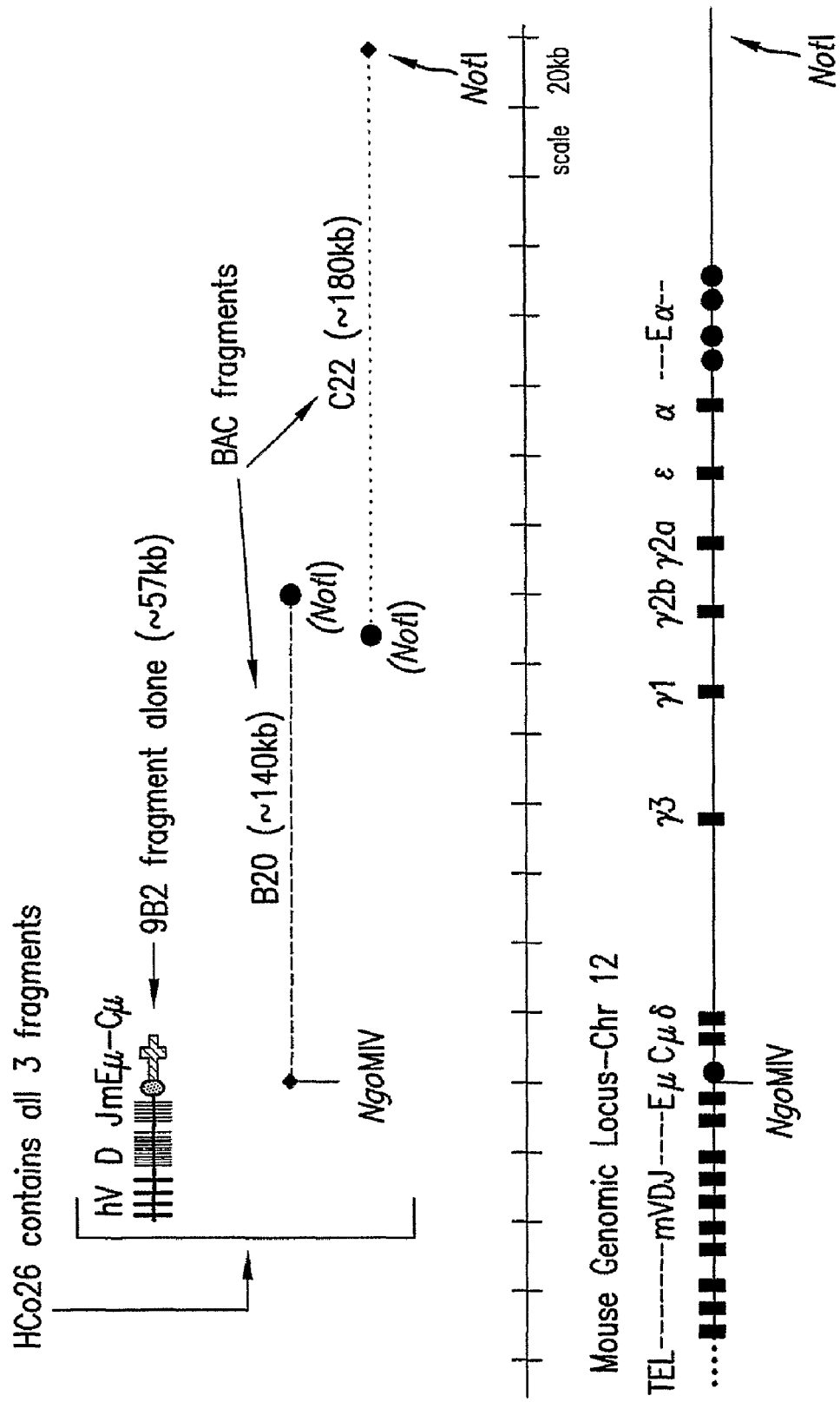
FIG. 1 is a schematic illustration of the 9B2 transgene construct and of the three fragments comprising the HCo26 transgene constructs aligned above the mouse genomic immunoglobulin locus.

This invention involves the use of a non-human transgenic animal that expresses chimeric antibodies as a host to raise a chimeric antibody to an antigen of interest, followed by conversion of the chimeric antibody to a fully human antibody. The chimeric antibodies expressed in the transgenic non-human host animal comprise human variable regions linked to constant regions of the non-human host animal. The invention pertains to transgene constructs, non-human transgenic host animals carrying such transgene constructs and methods of using such host animals to raise chimeric antibodies, which then can further be converted to fully human antibodies.

In order that the present invention may be more readily understood, certain terms are first defined. Additional definitions are set forth throughout the detailed description.

As used herein, the term "chimeric antibody" refers to an antibody in which at least one of the antibody chains (heavy or light) comprises variable regions sequences from one species (e.g., human) and constant region sequences from another species (e.g., mouse). The term "chimeric antibody" is intended to encompass antibodies in which: (i) the heavy chain is chimeric but the light chain comprises V and C regions from only one species; (ii) the light chain is chimeric but the heavy chain comprises V and C regions from only one species; and (iii) both the heavy chain and the light chain are chimeric.

As used herein, the term "transgene construct" refers to a nucleic acid preparation suitable for introduction into the genome of a host animal. A "transgene construct" of the invention can comprise a single piece of nucleic acid (such as the 9B2 transgene) or multiple pieces of nucleic acid (such as the HCo26 transgene). When the transgene construct comprises multiple pieces of nucleic acid, the individual pieces making up the transgene construct preparation contain overlapping sequences such that when they are introduced into the genome of the host animal, they recombine to create a contiguous transgene (see, for example, the further description of the HCo26 transgene herein).

As used herein, the term "isotype switching" refers to the phenomenon by which the class, or isotype, of an antibody changes from one Ig class to another Ig class through a recombination process mediated by switch sequences.

As used herein, a "nonswitched isotype" refers to the isotypic class of the heavy chain that is produced when no isotype switching has taken place. The $C_H$ gene encoding the nonswitched isotype is typically the first $C_H$ gene immediately downstream from the functionally rearranged VDJ gene (e.g., the IgM isotype).

As used herein, the term "switch sequence" or "switch region" refers to those DNA sequences, known in the art, that are responsible for switch recombination resulting in Ig class switching.

As used herein, the term "trans-switching" refers to isotype switching that involves recombination between one switch region and another switch region located on a different chromosome, such as recombination between a transgene switch region and an endogenous switch region located on a different chromosome than the chromosome that harbors the transgene. In particular, it refers to recombination between a transgene switch region and a switch region of the endogenous Ig constant region of the non-human transgenic host animal.

As used herein, the term "cis-switching" refers to isotype switching that involves recombination between one switch region and another switch region located on the same chromosome, such as recombination between two switch regions within a transgene or between two switch regions of the endogenous Ig locus, such as switch recombination between a μ constant region and a γ constant region carried by the same transgene or by the endogenous Ig locus.

As used herein the term "unrearranged" or "germline configuration" in reference to an immunoglobulin V segment refers to the configuration wherein the V segment is not recombined so as to be immediately adjacent to a D or J segment.

As used herein, the term "rearranged" in reference to an immunoglobulin V segment refers to the configuration wherein the V segment is positioned immediately adjacent to a D-J or J segment so as to encode essentially a complete $V_H$ or $V_L$ domain, respectively.

As used herein, the term "a plurality of unrearranged immunoglobulin (Ig) variable region sequences" is intended to refer to constructs that contain more than one heavy or light chain variable region segment in an unrearranged configuration.

As used herein, the term "operatively linked" is intended to describe the configuration of a nucleic acid sequence that is placed into a functional relationship with another nucleic acid sequence. For example, a promoter or enhancer is operatively linked to a coding sequence if it affects the transcription of the sequence. With respect to the joining of two protein coding regions, operatively linked means that the nucleic acid sequences being linked are contiguous and in reading frame. For switch sequences, operatively linked means that the sequences are capable of effecting switch recombination.

I. Transgene Constructs for Expressing Chimeric Antibodies

The transgene constructs of the invention comprise a plurality of unrearranged human immunoglobulin (Ig) variable region sequences operatively linked to at least one immunoglobulin (Ig) constant region sequence of a non-human host animal, wherein the transgene construct undergoes rearrangement in the non-human host animal and expresses chimeric antibodies in the non-human host animal, the chimeric antibodies comprising a human variable region and a constant region of the non-human host animal. In this context, the term "at least one Ig constant region sequence" is intended to mean a sequence encoding at least one constant region isotype sequence, such as an IgM constant region sequence or a kappa constant region sequence. The invention encompasses transgene constructs encoding chimeric heavy chain sequences or encoding chimeric light chain sequences. When integrated into a non-human transgenic host animal, the variable regions of the transgene constructs undergo rearrangement such that functional heavy chain or light chain variable regions are created. Moreover, in certain embodiments, the integrated transgene construct undergoes trans-switching such that chimeric antibodies of more than one isotype are made in the transgenic non-human host animal. When the transgene construct encodes chimeric heavy chain sequences, it comprises at least the IgM constant region of the non-human host animal and may contain additional host constant regions although, as demonstrated herein, the presence of the host IgM constant region alone, even without the known 3' IgH enhancers, is sufficient to secure maturation of the B cells and achieve trans-switching.

Accordingly, in one aspect, the plurality of unrearranged human Ig variable region sequences in the transgene construct are heavy chain variable region sequences. In particular, such heavy chain constructs typically comprise unrearranged human heavy chain V-D-J sequences. Such heavy chain constructs also contain at least one Ig constant region sequence of a non-human host animal and typically also contain regulatory sequences including enhancers and switch sequences. Thus, in a preferred embodiment, the transgene construct comprises, in 5' to 3' direction, a plurality of human $V_H$ regions, a plurality of human D segments, a plurality of human $J_H$ segments, a J-µ enhancer from a non-human host animal, a µ switch region from a non-human host animal and a µ constant region from a non-human host animal. In a particularly preferred embodiment, the construct comprises four human $V_H$ regions, 15 human D segments and six human $J_H$ segments, as described further in the Examples. A preferred but non-limiting example of a heavy chain construct of the invention is the 9B2 transgene.

Preferably, the heavy chain construct of the invention is capable, when integrated into a non-human host animal genome, of undergoing trans-switching with an endogenous constant region of the non-human host animal. As demonstrated herein, the presence in the transgene construct of the µ switch region and the µ constant region of the non-human host animal is sufficient to allow for trans-switching to occur between the integrated transgene and endogenous constant region sequences in the host animal. Thus, a heavy chain construct of the invention that comprises only one host animal constant region sequence, µ, can nevertheless lead to the generation of chimeric antibodies of multiple isotypes (e.g., IgM and IgG) in the host animal as a result of trans-switching.

Thus, another preferred transgene construct of the invention comprises, in 5' to 3' direction, a plurality of human $V_H$ regions, a plurality of human D segments, a plurality of human $J_H$ segments, a mouse J-µ enhancer, a mouse µ switch region and a mouse µ constant region, wherein the transgene construct, when integrated into a mouse genome, undergoes trans-switching with an endogenous mouse γ constant region such that chimeric antibodies comprising human V regions and mouse constant regions of IgM and IgG isotype are produced in the mouse.

While the presence of the µ constant region (and associated switch sequences) alone may be sufficient for the generation of multiple isotypes of chimeric antibodies, in certain instances it may be desirable to include more than one host animal constant region sequence in the heavy chain transgene construct such that both trans-switching and cis-switching can occur. Accordingly, in various embodiments, a heavy chain transgene construct of the invention may comprise one, two, three or more constant regions of the non-human host animal. For example, in another embodiment, in addition to the µ constant region, the construct can further comprise a γ constant region (and associated switch sequences) from a non-human host animal. For example, when a mouse is used as the transgenic non-human host animal, the heavy chain transgene construct can include murine p coding sequences (and associated switch sequences) and, additionally, can include one or more of the murine γ1, γ2a, γ2b and γ3 coding sequences (and associated switch sequences). In yet another embodiment, the construct can comprise all immunoglobulin (Ig) constant regions of the non-human host animal (i.e., the construct contains the entire C region of the non-human host animal, encompassing the µ, δ, γ, α, and ε constant sequences).

In another aspect, a transgene construct of the invention comprises a plurality of unrearranged human light chain variable region sequences, linked to a light chain constant region sequence of the non-human transgenic host animal. In particular, such light chain constructs typically comprise unrearranged human light chain V-J sequences, either kappa V-J sequences or lambda V-J sequences. In a preferred embodiment, the chimeric construct is a chimeric kappa light chain construct comprising, in 5' to 3' direction, a plurality of human $V_\kappa$ regions, a plurality of human $J_\kappa$ segments, a J-κ enhancer from a non-human host animal (e.g., the mouse κ internal enhancer) and a $C_\kappa$ coding region from a non-human host animal.

In another embodiment, the chimeric light chain construct can be a lambda light chain construct. In both the mouse and human Ig loci, there is a cluster of multiple $V_\lambda$ genes followed by repeated clusters of $J_\lambda$-$C_\lambda$ units. Thus, in one embodiment, a chimeric lambda chain transgene can be constructed by linking a plurality of human $V_\lambda$ regions to a plurality of human $J_\lambda$-non-human $C_\lambda$ combination units. Alternatively, one can select a single human $J_\lambda$-non-human $C_\lambda$ placed downstream of a plurality of human $V_\lambda$ regions. Another possible configuration is to place a plurality of human $V_\lambda$ regions upstream of the endogenous non-human $J_\lambda$-$C_\lambda$ clusters, which would lead to chimeric antibodies comprising a human $V_\lambda$ region linked to a non-human $J_\lambda$ region and a non-human $C_\lambda$ region.

The transgene constructs of the invention can be prepared using standard recombinant DNA techniques. Cloning vectors containing polylinkers are useful as starting vectors for insertion of DNA fragments of interest. Non-limiting examples of such suitable cloning vectors are described in the Examples. Plasmids or other vectors (e.g., YACs) carrying human unrearranged heavy chain or light chain immunoglobulin sequences have been described in the art (see e.g., U.S. Pat. Nos. 5,545,806; 5,569,825; 5,625,126; 5,633,425; 5,789, 650; 5,877,397; 5,661,016; 5,814,318; 5,874,299; and 5,770, 429; all to Lonberg and Kay; and 5,939,598; 6,075,181; 6,114,598; 6, 150,584 and 6,162,963, all to Kucherlapati et al.) Such plasmids and other vectors can be used as the source of human unrearranged heavy chain or light chain variable regions to be included in the transgene constructs of the invention. Additionally or alternatively, suitable human Ig variable region DNA can be obtained from genomic libraries using standard techniques. DNA encoding constant region sequences of the non-human host animal, including the coding sequences of the constant region and the associated enhancer and switch regions, similarly can be obtained from genomic libraries using standard techniques. For example, the B6 BAC library (Invitrogen) of murine genomic DNA can be used as the source of murine constant region sequences for inclusion in the transgene constructs of the invention.

In addition to the variable and constant coding regions, cis-acting regulatory sequences typically are needed for chromatin accessibility, proper V(D)J recombination, class switching, high levels of antibody expression and other locus control functions. Promoter regions located near the V(D)J gene segments may play a role in chromatin accessibility and V(D)J recombination. Intronic enhancers between the $J_H$ and IgM coding region and $J_\kappa$ and kappa coding regions have been identified. Additionally, downstream 3' DNase hypersensitivity regions have been identified, which make up the IgH locus control region (LCR). Class switch recombination is dependent on promoters and sterile transcripts of switch regions upstream of the different heavy chain constant regions. An origin of replication has also been identified downstream of the 3' DNase hypersensitive sites which may demark a boundary for the IgH locus. Preferably, the constructs of the invention contain at least the promoter regions located near the V(D)J gene segments, one or more operative switch regions and an intronic enhancer. Inclusion of all genomic DNA from the 5' intronic enhancers through downstream 3' LCRs, and possibly beyond, may be preferred (but not essential) for high levels of Ab generation, development and maturation.

The appropriate genomic DNA fragments from the human Ig variable regions and from the non-human host animal Ig constant regions are then operatively linked through ligation into a cloning vector, followed by characterization of the vector (e.g., by restriction fragment analysis or sequencing or the like) to ensure proper arrangement of the genomic fragments. A non-limiting example of the creation of a heavy chain transgene construct of the invention is described in detail in Example 1.

To prepare the transgene construct for microinjection or other technique for transgenesis, the transgene construct can be isolated from the vector in which it is carried by cleavage with appropriate restriction enzymes to release the transgene construct fragment. The fragment can be isolated using standard techniques, such as by pulse field gel electrophoresis on an agarose gel, followed by isolation of the fragment from the agarose gel, such as by β-agarase digestion or by electroelution. For example, the agarose gel slice containing the transgene construct fragment can be excised from the gel and the agarose can be digested with β-agarase (e.g., from Takara), using standard methodology.

II. Preparation and Characterization of Transgenic Non-Human Host Animals

Another aspect of the invention pertains to a transgenic non-human host animal that comprises one or more of the transgene constructs of the invention (i.e., the transgene construct(s) is integrated into the genome of the host animal), such that the animal expresses chimeric antibodies comprising human Ig variable regions and non-human host animal Ig constant regions. Preferably, the transgene construct undergoes trans-switching and the animal expresses chimeric antibodies comprising human Ig variable regions and non-human host animal Ig constant regions of at least IgM and IgG isotypes.

The transgenic non-human host animals of the invention are prepared using standard methods known in the art for introducing exogenous nucleic acid into the genome of a non-human animal. Preferred non-human animals are mice, although other animal species that are (i) suitable for transgenesis and (ii) capable of rearranging immunoglobulin gene segments to produce an antibody response may also be used. Examples of such species include but are not limited to rats, rabbits, chickens, goats, pigs, sheep and cows.

A preferred method for preparing the transgenic non-human animal, in particular a transgenic mouse, is that of pronuclear microinjection. This technology has been known for over twenty years and is well established (see e.g., Wagner, T. E. et al. (1981) *Proc. Natl. Acad. Sci. USA* 78:6376-6380; U.S. Pat. No. 4,873,191 by Wagner and Hoppe). In general, the method involves introducing exogenous genetic material into the pronucleus of a mammalian zygote (e.g., mouse zygote) by microinjection to obtain a genetically transformed zygote and then transplanting the genetically transformed zygote into a pseudopregnant female animal. The embryo is then allowed to develop to term and the genome of the resultant offspring is analyzed for the presence of the transgenic material. Southern blot analysis, PCR or other such technique for analyzing genomic DNA is used to detect the presence of a unique nucleic acid fragment that would not be present in the non-transgenic animal but would be present in the transgenic animal. Selective breeding of transgenic offspring allows for homozygosity of the transgene to be achieved.

Although the preferred embodiment of the invention comprises transgenic mice prepared by pronuclear microinjection, the invention encompasses other non-human host animals, including but not limited to rats, rabbits, pigs, goats, sheep, cows and chickens. Techniques for creating transgenic animals of each of these species have been described in the art.

For example, preparation of transgenic rats is described in Tesson, L. et al. (2005) *Transgenic Res.* 14:531-546, including by techniques such as DNA microinjection, lentiviral vector mediated DNA transfer into early embryos and sperm-mediated transgenesis. Methods of transgenesis in rats are also described in Mullin, L. J. et al. (2002) *Methods Mol. Biol.* 180:255-270.

Preparation of transgenic rabbits is described in, for example, Fan, J. et al. (1999) *Pathol. Int.* 49:583-594; Fan, J. and Watanabe, T. (2000) *J. Atheroscler. Thromb.* 7:26-32; Bosze, Z. et al. (2003) *Transgenic Res.* 12:541-553.

Preparation of transgenic pigs is described in, for example, Zhou, C. Y. et al. (2002) *Xenotransplantation* 9:183-190; Vodicka, P. et al. (2005) *Ann. N.Y. Acad. Sci.* 1049:161-171. Alternative transgenesis techniques to pronuclear microinjection in pigs include adenovirus mediated introduction of DNA into pig sperm (see e.g., Farre, L. et al. (1999) *Mol. Reprod. Dev.* 53:149-158) and linker-based sperm-mediated gene transfer (Chang, K. et al. (2002) *BMC Biotechnol.* 2:5).

Preparation of transgenic goats is described in, for example, Ebert, K. M. et al. (1991) *Biotechnology* (NY) 9:835-838; Baldassarre, H. et al. (2004) *Reprod. Fertil. Dev.* 16:465-470. Somatic cell nuclear transfer in goats is described in, for example, Behboodi, E. et al. (2004) *Transgenic Res.* 13:215-224.

Preparation of transgenic sheep is described in, for example, Ward, K. A. and Brown, B. W. (1998) *Reprod. Fertil. Dev.* 10:659-665; Gou, K. M. et al. (2002) *Shi Yan Sheng Wu Xue Bao* 35:103-108

Preparation of transgenic cows is described in, for example, Donovan, D. M. et al. (2005) *Transgenic Res.* 14:563-567. Gene transfection of donor cells for nuclear transfer of bovine embryos is described in, for example, Lee S. L. et al. (2005) *Mol. Reprod. Dev.* 72:191-200.

The state of the art in the preparation of transgenic domestic farm animals is also reviewed in Niemann, H. et al. (2005) *Rev. Sci. Tech.* 24:285-298.

Preparation of transgenic chickens is described in, for example, Pain, B. et al. (1999) *Cells Tissues Organs* 165:212-219; Lillico, S. G. et al. (2005) *Drug Discov. Today* 10:191-196. Use of retroviral vectors in the preparation of transgenic chickens is described in, for example, Ishii, Y. et al. (2004) *Dev. Dyn.* 229:630-642.

The transgenic non-human animals of the invention may comprise an Ig heavy chain transgene construct for expressing chimeric antibodies or an Ig light chain transgene construct for expressing chimeric antibodies, or both a light and a heavy chain construct for expressing chimeric antibodies. Typically, to create animals that carry more than one transgene, animals carrying individual transgenes are prepared and then cross-bred to create animals carrying more than one transgene. Animals that inherit both transgenes can be identified and selected by standard techniques for analysis of genomic DNA in the animals. Moreover, an animal of the invention carrying a transgene construct for expressing one chimeric Ig chain (e.g., a chimeric heavy chain) can be cross-bred with an animal that carries a transgene that expresses a non-chimeric form of the other Ig chain (e.g., a fully human light chain). In such animals, the antibodies expressed comprise one chimeric chain (e.g., a chimeric heavy chain) and one non-chimeric chain (e.g., a non-chimeric, fully human light chain). Such animals are also encompassed by the invention and suitable for use in raising chimeric antibodies against an antigen of interest. See the Examples for a further description of a transgenic animal expressing a chimeric heavy chain transgene construct and a fully human light chain transgene construct, wherein the chimeric heavy chain transgene construct undergoes trans-switching to produce antibodies of multiple isotypes (e.g., IgM and IgG) in the animals.

The non-human transgenic host animals of the invention express chimeric antibodies, in which at least one chain of the antibody comprises a human variable region sequence and a constant region sequence of the host animal. The non-human transgenic host animals of the invention do not express any fully human antibodies (comprising both a fully human heavy chain and a fully human light chain) since they do not carry both human constant region sequences (human $C_H$ and human $C_L$) in their genome. Thus, the antibody repertoire of these animals differs from that of the HuMab Mouse® (e.g., as described in PCT Publication WO 94/25585). Although the Ig transgenes in the HuMab Mouse® are described in WO 94/25585 as being capable of undergoing trans-switching with endogenous mouse Ig constant regions to create chimeric antibodies, the Ig transgenes in the HuMab Mouse® contain human variable region sequences and human constant region sequences and thus, in addition to possibly expressing chimeric antibodies, these mice also express a repertoire of fully human antibodies. In contrast, the transgenic non-human host animals of the present invention only express a repertoire of chimeric antibodies, without the additional presence of fully human antibodies in the animals.

Furthermore, the presence of constant regions of the non-human host animal in the chimeric antibodies expressed by the host animals is thought to allow for improved B cell and antibody development in vivo, as compared to transgenic animals that express antibodies having constant regions of another species (e.g., human constant regions). For example, the chimeric antibodies that contain host animal Fc regions are thought to associate better with endogenous host animal accessory proteins (e.g., Igα/Igβ or other signaling molecules) for more natural receptor signaling leading to more normal B cell development and higher antibody production. Moreover, the chimeric antibodies are thought to bind better to host Fc receptors, leading to increased recirculation and antigen presentation and, thus, more normal immune responses. Still further, the presence in the transgene construct of host animal regulatory sequences in the host animal-derived constant region is thought to lead to improved genetic regulation of antibody expression. Thus, such an environment in which there is more normal B cell development, more serum antibodies, improved genetic regulation of antibody expression and better germinal center formation should lead to a more diverse, and possibly higher affinity, antibody population with appropriate somatic mutations.

Thus, in certain embodiments, chimeric antibodies raised in the non-human transgenic host animals of the invention may exhibit increased somatic mutations as compared to fully human antibodies raised in non-human transgenic host animals. The presence of a constant region of the non-human host animal in the chimeric antibodies of the invention can also afford the advantage that the antibody may possess additional effector functions (e.g., ADCC, complement fixation) in the host animal species that would not be present with antibodies having human constant regions. Thus, a chimeric antibody raised according to the invention may be amenable for use in particular animal models of disease in which a fully human antibody may not be suitable for use. For example, chimeric antibodies raised according to the invention that comprise murine constant regions may be amenable for use in mouse models of disease that involve murine effector functions mediated by the murine Fc region.

In a preferred embodiment, a non-human transgenic host animal of the invention has one or more of its endogenous immunoglobulin loci inactivated. It is preferable that the endogenous Ig loci be inactivated so that endogenous host animal antibodies are not expressed in the animal together with the expression of the chimeric antibodies. In particular, inactivation of the endogenous Ig loci prevents interference from endogenous antibodies and simplifies the detection of the chimeric antibodies. Accordingly, in one embodiment, a transgenic host animal (e.g., mouse) of the invention has at least one endogenous heavy chain locus inactivated and more preferably has both endogenous heavy chain loci inactivated. Additionally or alternatively, the transgenic host animal (e.g., mouse) of the invention has at least one endogenous light chain locus inactivated and more preferably has both alleles of the kappa loci or the lambda loci, or both, inactivated. In the most preferred embodiment, the host animal has a homozygous inactivation of the endogenous Ig heavy chain locus and a homozygous inactivation of the endogenous Ig kappa light chain locus. When the kappa locus is inactivated, it is not essential to disrupt the lambda locus; however, if a chimeric lambda light chain transgene is to be used, it is desirable to inactivate the endogenous lambda locus.

The endogenous Ig loci are preferably inactivated by homologous recombination using a targeting vector that inserts an exogenous sequence into the endogenous Ig locus such that expression of the endogenous Ig genes is disrupted. Preferred regions for insertion are the $J_H$ and $J_\kappa$ regions. Once a host animal having a heterozygous disruption of a heavy chain or light chain locus is obtained, the animal can be bred to homozygosity for the disruption by standard breeding techniques. A mouse strain having a homozygous disruption of the endogenous heavy chain locus at $J_H$ has been previously described in the art (see e.g., Examples 10 and 11 of U.S. Pat. No. 5,545,806), as has a mouse strain having a homozygous disruption of the endogenous kappa light chain locus at $J_\kappa$ and $C_\kappa$ (see e.g., Example 9 of U.S. Pat. No. 5,545,806). Such mice can be used as breeding partners with mice carrying one or more transgenes of the invention to achieve a mouse strain carrying one or more transgenes and having its endogenous Ig loci inactivated. Such mouse strains are described in further detail in the Examples.

III. Preparation of Chimeric Antibodies in Transgenic Non-Human Animals

Another aspect of the invention pertains to method of making a chimeric antibody specific for an antigen of interest. The method comprises immunizing a transgenic non-human host animal of the invention with the antigen of interest and obtaining from the animal a chimeric antibody specific for the antigen of interest.

Thus, to prepare chimeric antibodies in a transgenic non-human animal of the invention, first the animal is immunized with an antigen of interest. For example, immunization techniques that have previously been used to raise fully human antibodies in transgenic mice carrying human Ig heavy and light chain transgenes (such as the HuMab Mouse® or the Xenomouse) can similarly be used to raise antibodies in the animals of the invention. Immunization techniques previously used in the HuMab Mouse® are described in, for example, Lonberg, N. et al. (1994) *Nature* 368:856-859; Fishwild, D. et al. (1996) *Nature Biotechnology* 14:845-851 and PCT Publications WO 98/24884 and WO 01/14424. Preferably, mice are 6-16 weeks of age upon the first infusion of antigen and a purified or recombinant preparation of antigen (e.g., 5-50 μg) is used to immunize the mice intraperitoneally. Typically, multiple animals (e.g., between 6 and 24 animals) are immunized for each antigen.

Cumulative experience with various antigens in the HuMab Mouse® have shown that the transgenic mice respond well when initially immunized intraperitoneally with antigen in complete Freund's adjuvant, followed by every other week IP immunizations (up to a total of 6) with antigen in incomplete Freund's adjuvant. However, adjuvants other than Freund's have also been found to be effective and can be used additionally or alternatively. The immune response can be monitored over the course of the immunization protocol with plasma samples being obtained by retroorbital bleeds. The plasma can be screened by ELISA and mice with sufficient titers against the antigen of interest can be used to prepare monoclonal antibodies. Mice can be boosted intravenously with antigen three days before sacrifice and removal of the spleen and/or lymph nodes.

Chimeric antibodies, as a polyclonal mixture, can be obtained from the host animal or, more preferably, monoclonal antibodies can be prepared using B cells obtained from the host animal. Monoclonal antibodies can be prepared and selected by one of a variety of suitable methods known in the art including, but not limited to, (i) hybridoma generation (discussed further below), (ii) PCR amplification of antibody genes directly from B cells of obtained from the host animal (see e.g., Babcook, J. S. et al. (1996) *Proc. Natl. Acad. Sci. USA* 93:7843-7848) and (iii) phage display of an antibody library prepared from B cells of the host animal, followed by screening of the phage display library for a monoclonal antibody of interest (see e.g., PCT Publication WO 01/25492)

In a preferred embodiment, hybridomas producing chimeric monoclonal antibodies of the invention are generated. To generate such hybridomas, splenocytes and/or lymph node cells from immunized mice can be isolated and fused to an appropriate immortalized cell line, such as a mouse myeloma cell line (e.g., P3x63-Ag8.653 (ATCC, CRL-1580) or SP2/0 (ATCC, CRL-1581)). Cells can be fused using techniques well established in the art, such as chemically-mediated fusion (e.g., with PEG) or electrofusion. Once extensive hybridoma growth has occurred, individual wells can be screened by ELISA For example, in animals expressing a chimeric Ig heavy chain transgene and a fully human kappa light chain transgene, wells can be screened by ELISA for expression of antibodies comprising mouse IgM and human kappa or mouse IgG and human kappa. Using similar techniques, the supernatants can be tested for the presence of mouse IgG that binds to the antigen used for immunization. Hybridomas positive for an antibody of interest can be subcloned at least twice by limiting dilution. The stable subclones can then be cultured in vitro to generate antibody material in tissue culture medium for further characterization.

IV. Conversion of Chimeric Antibodies to Fully Human Antibodies

In the methods of the invention, once a chimeric antibody of interest has been raised in the transgenic non-human host animal, the method can further comprise isolating from the animal, or a B cell from the animal, a nucleic acid encoding the chimeric antibody and replacing nucleic acid encoding the non-human host animal Ig constant region with nucleic acid encoding a human Ig constant region to thereby convert the chimeric antibody to a human antibody and expressing the human antibody.

Thus, once a chimeric antibody of interest has been identified, it can be converted to a fully human antibody using standard recombinant DNA techniques. For example, DNA encoding the variable region (light or heavy chain) from the chimeric antibody can be obtained by standard molecular biology techniques (e.g., PCR amplification or cDNA cloning using a hybridoma that expresses the antibody of interest) and the DNA can be inserted into an expression vector such that the variable region sequences are operatively linked to a human constant region sequence, as well as to transcriptional and translational control sequences. An antibody heavy chain gene and an antibody light chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). An expression vector can be used that already encodes heavy chain constant and light chain constant regions of the desired isotype such that the $V_H$ segment is operatively linked to the $C_H$ segment(s) within the vector and the $V_L$ segment is operatively linked to the $C_L$ segment within the vector. A non-limiting examples of suitable expression vectors for expressing fully human antibodies the pIE family of vectors as described in U.S. Patent Application No. 20050153394 by Black. Preferred constant region isotypes present in the expression vectors include human IgG1 and IgG4 constant regions for the heavy chain and the human kappa constant region for the light chain.

In the context of antibody expression vectors, the term "operatively linked" is intended to mean that an antibody variable region is ligated into the expression vector such that the coding sequences of the variable region are in-frame with the coding sequences of the constant region. Moreover, the variable and constant regions are positioned within the vector such that the transcriptional and translational control sequences within the vector serve their intended function of regulating the transcription and translation of the antibody gene. The expression vector and expression control sequences are chosen to be compatible with the expression host cell used. Additionally, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter) and polyoma. Alternatively, nonviral regulatory sequences may be used, such as the ubiquitin promoter or βglobin promoter. Still further, regulatory elements can be composed of sequences from different sources, such as the SRα promoter system, which contains sequences from the SV40 early promoter and the long terminal repeat of human T cell leukemia virus type 1 (Takebe, Y. et al (1988) *Mol. Cell. Biol.* 8:466-472).

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

Other sequences that can be included in the expression vector include those that enhance expression of the antibody genes in stable transfectants, such as sequences that alter chromatin structure to prevent silencing of the transfected gene. A preferred example is a UCOE (ubiquitous chromatin opening element), which can enhance expression of transfected sequences irrespective of their site of integration in a stable transfectant.

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The conversion of a chimeric antibody of the invention to a fully human antibody is described in further detail in Example 6. As demonstrated in that example, conversion of the chimeric form to the fully human form maintained the binding properties of the antibody toward its target antigen. In certain instances (such as in Example 6), the fully human form of the antibody may even exhibit improved binding toward its target, such as higher affinity toward its target than the chimeric form. Thus, in certain embodiments of the method for converting the chimeric antibody to a human antibody, the resultant human antibody exhibits higher affinity toward the antigen of interest than the original chimeric antibody.

EXAMPLES

In the following examples, certain plasmids, homologous recombinant mice and transgenic mice that have been previously described were used as starting materials to create additional transgenes and transgenic mouse strains.

Plasmids and DNA Clones:

The pGP1 and pGP2 are general cloning vectors whose construction is described in U.S. Pat. No. 5,545,806 (see in particular Example 4 and FIGS. 7 and 8). Both are pBR322-derived plasmids that have been modified to contain large polylinkers. In pGP1, the polylinker is flanked by rare cutting NotI sites for building large inserts. pGP2 was derived from pGP1 and includes an additional SfiI site located between the MluI and SpeI sites in the polylinker. pGP1b and pGP2b are similar pBR322-derived cloning vectors. The construction of pGP1b also is described in U.S. Pat. No. 5,545,806 (see, in particular, Example 12), whereas the construction of pGP2b is described in U.S. Pat. No. 5,625,126 (see, in particular, Example 36 and FIGS. 77A and 77B).

The pHC2 plasmid also is described in U.S. Pat. No. 5,545, 806 (see in particular Example 12 and FIGS. 25 and 31). pHC2 contains four functional human immunoglobulin heavy chain variable ($V_H$) regions, 15 human D segments, all six human $J_H$ segments, the human J-μ enhancer, human μ switch region, all of the human μ coding exons, and the human γ1 constant region, including the associated switch region and sterile transcript associated exons, together with 4 kb flanking sequencing upstream of the sterile transcript initiation site contained on a NotI fragment.

The RP23-109B20 (B20) genomic C57BL/6J mouse DNA clone was obtained from Invitrogen and contains mouse $J_H$ regions through mouse IgG2a coding regions. The RP23-

116C22 (C22) genomic C57BL/6J mouse DNA clone was also obtained from Invitrogen and contains mouse IgG2b coding regions and approximately 200 kb downstream of the mouse IgG2b coding regions.

Homologous Recombinant Mice:

Mice in which the endogenous immunoglobulin heavy chain locus and/or the endogenous immunoglobulin light chain locus have been disrupted by homologous recombination have been previously described. In these examples, mice were used in which: (i) the murine light chain $J_\kappa$ regions were deleted and replaced with the $neo^R$ gene (referred to herein as the "JKD" genotype); (ii) the murine heavy chain Cμ region was disrupted by insertion of the $neo^R$ gene in the opposite reading frame of the Cμ gene (referred to herein as the "CMD" genotype); and/or (iii) the murine heavy chain $J_H$ region was deleted and replaced with the $neo^R$ gene (referred to herein as the "JHD" genotype). Construction of mice carrying the JHD modification is described in Examples 10 and 11 of U.S. Pat. No. 5,545,806. Construction of mice carrying the CMD modification is described in Example 1 of U.S. Application No. 20020086014. Construction of mice carrying the JKD modification is described in Example 9 of U.S. Pat. No. 5,545,806.

Transgenic Mice:

Mice carrying an unrearranged human light chain immunoglobulin transgene, comprising multiple $V_\kappa$ regions, $J_\kappa$ regions and the entire human kappa constant region, have been described previously. In these examples, mice were used that carry the KCo5 light chain transgene, which was created by co-injection of a human kappa light chain minilocus and a YAC clone comprising multiple human $V_\kappa$ segments. Construction and characterization of mice strains carrying the KCo5 light chain transgene are described in detail in Example 38 of U.S. Pat. No. 6,255,458. Through breeding with the homologous recombinant mice strains described above, additional mice strains were obtained in which (i) the KCo5 transgene was present (KCo5+); (ii) the endogenous light chain gene had been disrupted (JKD+/+) and (iii) the endogenous heavy chain gene had been disrupted (either JHD+/+ or CMD+/+).

Example 1

Construction of a Chimeric Transgene For Expressing Chimeric Antibodies Comprising Human $V_H$ and Mouse $C_H$ Regions A transgene construct was prepared that contained unrearranged human heavy chain VDJ segments linked to the mouse Jμ enhancer region, μ switch region and μ coding region, as follows.

Intermediate Vectors

The intermediate vector pGP2-1 was constructed by digesting the previously described pGP2b with NotI, releasing the polylinker and ligating with a synthetic linker constructed by annealed overlapping oligos DMTM12 (5'-GGC-CGCACGCGTGTC GACTC-3') (SEQ ID NO: 1) and DMTM13 (5'-GCCGAGTCGACACGCGTGC-3') (SEQ ID NO: 2). The resulting pGP2-1 plasmid then has a polylinker with a NotI site followed by a MluI, and a SalI site. The orientation and linker sequence were confirmed by sequencing.

The intermediate vector pIM-m2 was constructed by digesting the previously described pGP1b with NotI, releasing the polylinker and ligating with a synthetic linker constructed by annealed overlapping oligos DMTM39 (5'-GGC-CGCATTCGCCGG CTAACGGCGCCTA TAACGAGTTC-3') (SEQ ID NO: 3) and DMTM40 (5'-GGCCGAACGGCTTATAGGCGCCG TTAGCCGGCGAATGC-3') (SEQ ID NO: 4). The resulting pIM-m2 plasmid then has a polylinker with a NotI site followed by a NgoMIV site, a NarI site, a MluI site.

The intermediate vector pIM-m3 was constructed by digesting the previously described pGP1b with XhoI and HindIII, releasing part of the polylinker and ligating with a synthetic linker constructed by annealed overlapping oligos DMTM37 (5'-TCGAGGCCGGCATGATAG GCGCCGTC-GACA-3') (SEQ ID NO: 5) and DMTM38 (5'-AGCTTGTC-GACGGCGCCTA TCATGCCGGCC-3') (SEQ ID NO: 6). The resulting pIM-m3 plasmid then has a polylinker with these sites: NotI-XhoI-NgoMIV-NarI-SalI-HindIII-NotI.

Construction of Chimeric Transgene pHC2 has a unique MluI restriction site located downstream of the most 3' human $J_H$ segment and 5' of the human J-μ enhancer. The approximately 44 kb NotI-MluI fragment from pHC2, containing four functional human variable regions, 15 human D segments and all six human $J_H$ segments, was isolated and cloned into the intermediate vector pGP2-1. The new plasmid (phVDJ2) was screened by observing an approximate 44 kb fragment released by NotI and MluI digestion and southern blot hybridization to a probe just 5' of the human J-μ enhancer.

To isolate the mouse J-μ enhancer, mouse μ switch region, all of the mouse μ coding regions and the mouse δ coding regions, the B20 BAC was digested with NgoMIV and NarI. The resulting 40 kb fragment was isolated by pulse field gel electrophoresis (PFGE) and cloned into pIM-m2. The resulting plasmid (pIM-m2-mED) was screened by the appearance of a PCR fragment using primers specific for mouse IgM and by observing an approximate 40 kb fragment released by NgoMIV and NarI digestion. Furthermore, the mouse μ switch region was checked by southern blot to be full length (as compared to the starting B20 BAC) as part of this region often becomes deleted.

To isolate the mouse J-μenhancer, mouse μ switch region, all of the mouse μ coding regions, pIM-m2-mED was digested with XhoI (located 3' of the mouse IgM coding region) and NarI and ligated with a synthetic linker constructed by annealed overlapping oligos DMTM72 (5'-TC-GACTCCGCGGTTTAAACTGG-3') (SEQ ID NO: 7) and DMTM73 (5'-GGCGCC AGTTTAAACCGCGGAG-3') (SEQ ID NO: 8). The new resulting plasmid (pIM-m2-mEM) contained the mouse J-μ enhancer, mouse μ switch region, all of the mouse μ coding regions on an approximate 13 kb NgoMIV-NarI fragment with no internal XhoI or SalI sites. pIM-m2-mEM was screened by the appearance of a PCR fragment using DMTM73 and DMTM76, which is specific for a region 5' of the XhoI site and points downstream towards the newly inserted linker.

The approximate 13 kb NgoMIV-NarI fragment, containing the mouse J-μ enhancer, mouse μ switch region and all of the mouse μ coding regions, was then cloned into pIM-m3 to create pIM-m3-mEM, which adds a 5' XhoI site and a 3' SalI site to the fragment. pIM-m3-mEM was screened by observing an 13 kb fragment released by NgoMIV and NarI digestion and by XhoI and SalI digestion.

The final phVDJ2-mEM construct was then constructed by ligating the 13 kb XhoI-SalI fragment, containing the mouse J-μ enhancer, mouse μ switch region and all of the mouse μ coding regions, from pIM-m3-mEM into the SalI site 3' of the human VDJ region in phVDJ2. Clones were checked for directional cloning by the production of a PRC product from DMTM79 (5'-GCTGGAAAGAGAACTGTCGGAGTGGG-3') (SEQ ID NO: 9), which anneals just downstream of the human $J_H$ region pointing downstream, and DMTM80 (5'-CCAAAGTCCC TATCCCATCATCCAGGG-3') (SEQ ID NO: 10), which anneals to the mouse J-μ enhancer and points upstream. Furthermore, the final clone of phVDJ2-mEM (called 9B2, illustrated schematically in FIG. 1) was checked by southern blot to contain the full length mouse μ switch region (as compared to the starting B20 BAC). The final construct thus contains the human VDJ regions of pHC2 upstream of the mouse J-μ enhancer, mouse μ switch region, and all of the mouse μ coding regions on an approximately 57 kb fragment.

Example 2

Preparation and Screening of Transgenic Mice

The approximately 57 kb NotI-SalI fragment from clone 9B2 of phVDJ-mEM (described in Example 1) was released from the vector and isolated by PFGE. An agarose gel slice with the 9B2 insert was excised and the agarose was digested with β-agarase (Takara) according to the manufacturer's protocol. The 9B2 fragment was micro-injected (by standard methods) into fertilized oocytes. DNA was injected into F1 mice of wild type (JHD−/− CMD−/−, JKD−/−, KCo5−)× KCo5 mice (JHD−/−, CMD+/+, JKD+/+, KCo5+/+). Potential founder mice were screened for the 9B2 transgene by PCR with DMTM79 and DMTM80 using tail DNA as template. There were 4 resulting founder mice (9B2-52, 9B2-56, 9B2-58, and 9B2-65) on the JHD−/−, CMD+/−, JKD+/−, KCo5+/− strain background.

Since mice of the CMD+/− genotype still carry the endogenous mouse heavy chain J region, it was desirable to breed these founder mice with mice carrying the JHD deletion to obtain mice of the genotype CMD −/−, JHD+/+. Thus, founder mice positive for the 9B2 transgene were then bred to JHD (KCo5) mice (JHD+/+, CMD−/−, JKD+/+, KCo5+/+ mice) and genotyped for 9B2, JHD, CMD, JKD and KCo5.

To generate 9B2 transgenic animals on the appropriate strain background: (9B2+, JHD+/+(CMD−/−), JKD+/+, KCo5+), founder offspring were selected in part by their genotype (how similar they were to the final desired strain configuration) and if they were shown to have any pre-immune mouse IgG, or seemingly elevated post immunization mouse IgG levels. Offspring that carried either JHD+/+ (knock out for mouse $J_H$ region) or JHD+/− and CMD+/− (functionally knocked out for mouse heavy chain production) on a JKD+/+ and KCo5+ background were pre-immune titered for total mouse IgG/human kappa and mouse IgM/human kappa. The mice were then challenged with Tetanus Toxiod (TT) at 1-2 week intervals, with 50 μg of TT and 25 μg of Keyhole Limpet Hemocyanin (KLH) in 100 μl total volume of RIBI adjuvant, and titered for mouse IgG/human kappa, mouse IgM/human kappa and TT specific mouse IgG levels 10 days post the final immunization. Breeding continued for each founder line in this manner until 9B2+, JHD+/+ (CMD−/−) JKD+/+ strains were achieved.

Four founder lines carrying the 9B2 transgene were achieved, 9B2-52, 9B2-56, 9B2-58 and 9B2-65. Each 9B2 founder line transmits the transgene in a Mendelian manner and the transgene is not linked to the sex chromosomes, or any obvious physical coat coloration genes.

Example 3

Characterization of Transgenic Mice Expressing Chimeric Antibodies

In this example, the antibody responses of the four transgenic mice founder lines described in Example 2 to tetanus toxoid (TT) and Interferon-α (IFN-α) were examined to identify mice expressing high levels of antibodies in which a human kappa light chain was paired with a heavy chain having a mouse IgG constant region, indicating that the heavy chain used in the antibody was derived from the transgene construct that had undergone rearrangement and trans-switching with the endogenous mouse IgG constant region.

Tetanus Toxoid Responses

The antibody responses to TT for the four 9B2 mouse lines were examined as follows. Five or six mice of each strain, consisting of four to five transgenic positive mice and at least one non-transgenic (ntg) mouse for use as a negative control, were challenged weekly with TT at 50 μg of TT in 100 μl total volume of RIBI adjuvant for four weeks. Sera were titered for mouse IgG/human kappa, mouse IgM/human kappa and TT-specific mouse IgG levels 10 days after the final immunization. Other controls were the HC2 HuMab strain (carrying a fully human heavy chain transgene, pHC2 where the human $V_H$, D and $J_H$ gene segments are the same as in the 9B2, and a fully human light chain transgene) and the B6 wild-type mouse strain.

Table 1 below summarizes the titer levels for each mouse within the cohort, along with the non-transgenic controls, the HC2 strain and the B6 strain. The results shown for the 9B2 strains are the pre-immunization (naive) serum levels of total mouse IgG/human kappa antibodies in μg/ml (column 3), the preimmune levels of total mouse IgM/human kappa antibodies in μg/ml (column 4), the post-immunization serum levels of total mouse IgG/human kappa antibodies in μg/ml (column 5), the post-immunization serum levels of total mouse IgM/human kappa antibodies at lowest titer dilution at 3× background (column 6) and TT specific/mouse gamma antibodies in μg/ml (column 7). The appropriate analogous results are also shown for the HC2 and B6 strains.

TABLE 1

Serum Titers of TT Immunized Transgenic Mice

| | | preimmune | | post 4 IMS hK/mM | | |
|---|---|---|---|---|---|---|
| Line | Mouse ID# | mG/hK (μg/ml) | hK/mM (μg/ml) | mG/hK (μg/ml) | (titer-3xbkgd) | TT/mG (μg/ml) |
| 9B2-52 | 98683 | 5.2 | 14.5 | 21.3 | 1620 | 7.7 |
| | 98684 | 0.6 | 9.8 | 2.6 | 1620 | 0.3 |
| | 98929 | 1.9 | 54.3 | 40.5 | 14580 | 34.6 |
| | 98930 | 1.4 | 21.5 | 16.1 | 4860 | 0.0 |
| | 98931 | 0.0 | 17.0 | 0.2 | 4860 | 0.0 |
| | 99746-ntg | 0.0 | 0.0 | 0.0 | 0 | 0.0 |

TABLE 1-continued

Serum Titers of TT Immunized Transgenic Mice

| Line | Mouse ID# | preimmune mG/hK (µg/ml) | preimmune hK/mM (µg/ml) | post 4 IMS mG/hK (µg/ml) | post 4 IMS hK/mM (titer-3xbkgd) | post 4 IMS TT/mG (µg/ml) |
|---|---|---|---|---|---|---|
| 9B2-56 | 92986 | 0.2 | 317.7 | 0.5 | 43740 | 0.0 |
|  | 93382 | 0.4 | 199.3 | 1.3 | 43740 | 0.0 |
|  | 98693 | 1.6 | 164.5 | 2.4 | 43740 | 0.3 |
|  | 98694 | 0.4 | 183.7 | 0.2 | 43740 | 0.2 |
|  | 98695 | 0.2 | 138.4 | 0.5 | 14580 | 24.3 |
|  | 98697-ntg | 0.0 | 0.5 | 0.0 | 0 | 0.0 |
| 9B2-58 | 96339 | 1.9 | 103.9 | 56.8 | 14580 | 48.1 |
|  | 94744 | 0.6 | 94.9 | 6.9 | 14580 | 13.6 |
|  | 96042 | 0.9 | 230.0 | 15.0 | 43740 | 4.6 |
|  | 97942 | 1.7 | 194.9 | 93.2 | 43740 | 24.2 |
|  | 97944 | 2.5 | 137.4 | 163.9 | 43740 | 67.7 |
|  | 97945-ntg | 0.0 | 0.0 | 0.0 | 0 | 0.0 |
| 9B2-65 | 99770 | 1.1 | 11.8 | 3.5 | 4860 | 0.0 |
|  | 99771 | 6.0 | 11.8 | 21.2 | 4860 | 0.5 |
|  | 99775 | 18.9 | 18.7 | 36.0 | 60 | 0.3 |
|  | 99777 | 2.3 | 21.7 | 5.6 | 1620 | 0.0 |
|  | 99776 | 0.1 | 0.0 | 0.0 | 0 | 0.0 |
|  | 99778-ntg | 0.2 | 0.0 | 0.0 | 0 | 0.0 |
|  |  | hG/hk (µg/ml) | hk/hM (titer) | hG/hk (µg/ml) | hk/hM (titer) | TT/hG (µg/ml) |
| HC2 | 98679 | 100.5 | 1620 | 56.9 | 1920 | 0.2 |
|  | 98680 | 31.4 | 1620 | 57.1 | 4860 | 2.4 |
|  | 98681 | 23.6 | 1620 | 84.5 | 4860 | 0.6 |
|  |  | mG/mK (titer) | mK/mM (titer) | mG/mK (µg/ml) | mK/mM (titer) | TT/mG (µg/ml) |
| B6 | 99898 | 180 | 43740 | 14580 | 43740 | 72712.1 |
|  | 99899 | 180 | 43740 | 14580 | 43740 | 147832.0 |
|  | 99900 | 180 | 43740 | 14580 | 43740 | 38433.8 |

As expected, non-transgenic mice from each line do not express any mouse IgM/human kappa or mouse IgG/human kappa antibodies pre or post immunization. In the transgenic mice, expression of mouse IgM/human kappa antibodies is believed to be a result of rearrangement of the transgenic human VDJ segments to form a functional V region and splicing to the downstream transgenic mouse IgM constant region. Furthermore, in the transgenic mice, mouse IgG/human kappa antibodies are believed to be trans-switched antibodies containing rearranged transgenic human VDJ regions trans-switched to endogenous mouse IgG constant regions.

As the results in Table 1 demonstrate, lines 9B2-52 and 9B2-56 have low levels of naïve mouse IgG (trans-switched antibodies) and mouse IgM (derived from the transgene), whereas lines 9B2-58 and 9B2-65 contained higher levels of mouse IgG antibodies in naïve serum. Furthermore, lines 9B2-58 and 9B2-65 had elevated serum titers of mouse IgG/human kappa antibodies after immunization. All the mice tested for line 9B2-58 expressed TT-specific mouse IgG, whereas the results were more variable for the other lines, with some of the tested mice expressing TT specific mouse IgG post immunization and others not. The HC2 HuMab strain also showed variability in the TT-specific responses of individual mice. In some mice, levels of TT specific mouse IgG in sera were higher than levels of total mouse IgG/human kappa in sera. It is thought that this may represent sera containing TT specific mouse IgG paired with an endogenous mouse lambda light chain.

Splenocytes from one TT immunized 9B2-58 mouse were fused via electrofusion and TT specific hybridomas were produced. The hybridomas were stable and 12 hybridomas making anti-TT antibodies were initially isolated. Further cDNA sequence, protein characterization and BIACORE analysis were performed on antibodies from nine of the hybridomas. Supernatants from the hybridomas were used in a BIACORE experiment to determine affinity to TT, as well as on-rates and off-rates. For comparison, a fully human anti-TT antibody (raised in a HuMab Mouse® and expressed in CHO cells) was used (referred to as TT hu IgG), as well as a recombinantly-produced chimeric mouse IgG/human kappa antibody (expressed in CHO cells) which contains the same human VDJ and human kappa chain as the TT hu IgG. Results of the affinity, on-rate and off-rate comparison are shown in Table 2 below. Hybridoma clone names are in column 1 while BIACORE data are in columns 2-4.

TABLE 2

BIACORE Analysis of Antibodies from TT Immunized Transgenic Mice

| Clone Name | Affinity (nM) | On-rate (1/Ms) × $10^4$ | Off-rate (1/s) × $10^4$ |
|---|---|---|---|
| 43H7C10 | 22.4 | 3.9 | 8.8 |
| 43C4E8 | 23.1 | 4 | 9.2 |
| 41A7B2 | 29 | 3.8 | 1.1 |
| 7G7A9 | 141 | 3.3 | 46 |
| 14D6G4 | 100 | 3.4 | 34 |
| 24F10A8 | 122 | 3.3 | 40 |
| 40G8F2 | 134 | 3.2 | 43 |
| 50C1G4 | 139 | 2.9 | 40 |

TABLE 2-continued

BIACORE Analysis of Antibodies from
TT Immunized Transgenic Mice

| Clone Name | Affinity (nM) | On-rate (1/Ms) × 10^4 | Off-rate (1/s) × 10^4 |
|---|---|---|---|
| 49A1A6 | 293 | 0.18 | 5.4 |
| hu anti-TT | 52 | 1.9 | 9.7 |
| chi anti-TT | 82 | 2.1 | 17 |

This data demonstrates that the chimeric anti-TT antibodies raised in the transgenic mice have comparable affinities, on-rates and off-rates as the fully human anti-TT antibody and the recombinantly-created chimeric antibody made from the fully human anti-TT antibody. In fact, several of the chimeric antibodies raised in the 9B2-58 mouse have higher affinities than the one fully human anti-TT antibody studied.

IFN-α Responses

To examine the antibody responses of the transgenic mice to IFN-α, six to thirteen mice (five to eleven transgenic mice from each strain, and at least one non-transgenic mouse for use as a negative control) were challenged weekly with 20 μg of IFN-α in 100 μl total volume of RIBI adjuvant. Serum was titered for mouse IgG/human kappa, mouse IgM/human kappa and IFN-α-specific mouse IgG levels 10 days post four and seven immunizations.

Table 3 below summarizes the titer levels for each mouse within the cohort, along with the non-transgenic controls. The results shown are the pre-immunization (naive) serum levels of total mouse IgG/human kappa antibodies in μg/ml (column 3), the preimmune levels of total mouse IgM/human kappa antibodies in μg/ml (column 4), the post-4 immunization serum levels of total mouse IgG/human kappa antibodies in μg/ml (column 5), the post-4 immunization serum levels of total mouse IgM/human kappa antibodies in μg/ml (column 6), IFN-α specific/mouse gamma antibodies at lowest titer dilution at 3× background (column 7), the post-7 immunization serum levels of total mouse IgG/human kappa antibodies in μg/ml (column 8), the post-7 immunization serum levels of total mouse IgM/human kappa antibodies in μg/ml (column 9) and IFN-α specific/mouse gamma antibodies at lowest titer dilution at 3× background (column 10).

TABLE 3

Serum Titers of IFN-α Immunized Transgenic Mice

| | | Preimmune | | post 4 IM | | | post 7IM | | |
|---|---|---|---|---|---|---|---|---|---|
| line | mouse | Total mG/hK (μg/ml) | Total hK/mM (μg/ml) | Total mG/hK (μg/ml) | Total hK/mM (μg/ml) | INFA/mG (titer-3Xbkgd) | Total mG/hK (μg/ml) | Total hK/mM (μg/ml) | INFA/mG (titer-3Xbkgd) |
| 9B2-52 | 82441 | 1.6 | 107.4 | 4.2 | 130.3 | 60 | 11.2 | 117.7 | 0 |
| | 82444 | 1.0 | 64.8 | DM | | | | | |
| | 84028 | 1.6 | 107.7 | 7.7 | 106.7 | 540 | 8.2 | 47.6 | 0 |
| | 84029 | 1.4 | 77.5 | 1.1 | 51.9 | 20 | 1.2 | 40.3 | 0 |
| | 84184 | 6.8 | 25.1 | 35.8 | 54.7 | 1620 | 22.8 | 49.9 | 162 0 |
| | 84030-ntg | 0.0 | 0.0 | 0.0 | 0.0 | 0.0 | 0.0 | 0.0 | 0.0 |
| 9B2-56 | 87314 | 0.6 | 174.4 | 1.9 | 111.9 | 540.0 | 2.6 | 268.7 | 0.0 |
| | 87315 | 0.2 | 139.2 | 0.2 | 80.1 | 180.0 | 0.2 | 238.1 | 0.0 |
| | 87316 | 0.1 | 519.9 | 0.2 | 164.7 | 180.0 | 0.1 | 559.0 | 0.0 |
| | 87320 | 0.0 | 162.2 | 0.2 | 169.6 | 0.0 | 0.3 | 344.0 | 0.0 |
| | 87321 | 0.9 | 165.3 | 4.1 | 385.1 | 0.0 | 0.2 | 720.6 | 0.0 |
| | 89425-ntg | 0.0 | 0.0 | 0.0 | 0.0 | 0.0 | 0.0 | 0.0 | 0.0 |
| 9B2-58 | 78744 | 2.9 | 64.9 | 66.7 | 264.5 | 4860.0 | 178.4 | 47.4 | 437 40.0 |
| | 78751 | 0.9 | 170.6 | 96.2 | 326.9 | 4860.0 | 4.5 | 126.1 | 486 0.0 |
| | 78754 | 5.3 | 132.6 | 9.6 | 381.4 | 1620.0 | 181.6 | 494.5 | 145 80.0 |
| | 81198 | 5.8 | 94.2 | 24.1 | 243.2 | 4860.0 | 16.9 | 168.4 | 437 40.0 |
| | 80620 | 7.8 | 169.7 | 27.5 | 360.8 | 14580.0 | 444.5 | 1043.1 | 437 40.0 |
| | 80623 | 2.8 | 139.4 | 17.2 | 368.3 | 4860.0 | 86.4 | 166.5 | 145 80.0 |
| | 80624 | 9.8 | 133.6 | 323.6 | 380.0 | 43740.0 | 1694.6 | 45.9 | 437 40.0 |
| | 80460 | 5.8 | 89.5 | 24.0 | 0.8 | 4860.0 | DM | | |
| | 80461 | 3.1 | 217.2 | 12.8 | 385.6 | 4860.0 | 45.6 | 679.7 | 145 80.0 |
| | 80468 | 9.3 | 62.7 | 40.1 | 151.1 | 1620.0 | 176.1 | 115.5 | 437 40.0 |
| | 80473 | 1.8 | 102.7 | 16.5 | 159.5 | 1620.0 | 38.3 | 368.7 | 437 40.0 |
| | 78752-ntg | 0.0 | 0.0 | 0.0 | 0.0 | 0.0 | 0.0 | 0.0 | 0.0 |
| | 80621-ntg | 0.0 | 0.0 | 0.0 | 0.0 | 0.0 | 0.0 | 0.0 | 0.0 |
| 9B2-65 | 97143 | 1.0 | 12.1 | 5.1 | 5.8 | 0.0 | | not done | |
| | 97955 | 263.2 | 19.5 | 68.7 | 14.1 | 0.0 | | | |
| | 97957 | 27.7 | 15.4 | 72.8 | 12.5 | 0.0 | | | |
| | 97959 | 2899.0 | 19.9 | 1878.0 | 15.8 | 50.0 | | | |
| | 97961 | 136.3 | 29.1 | 32.8 | 18.1 | 100.0 | | | |
| | 97144-ntg | 0.0 | 0.0 | 0.0 | 0.0 | 0 | | | |

DM = dead mouse

Again as expected, non-transgenic (ntg) mice from each line do not express any mouse IgM/human kappa or mouse IgG/human kappa antibodies pre or post immunization. In the IFN-α immunized transgenic mice, expression of mouse IgM/human kappa antibodies is believed to be a result of rearrangement of the transgenic human VDJ segments to form a functional V region and splicing to the downstream transgenic mouse IgM constant region. Furthermore, in the transgenic mice, mouse IgG/human kappa antibodies are believed to be trans-switched antibodies containing rearranged transgenic human VDJ regions trans-switched to endogenous mouse IgG constant regions.

Similar to the results for the TT responses, lines 9B2-52 and 9B2-56 have low levels of naïve mouse IgG (trans-switched antibodies) and mouse IgM (derived from the transgene), whereas lines 9B2-58 and 9B2-65 contained higher levels of mouse IgG antibodies in naïve serum. Furthermore, lines 9B2-58 and 9B2-65 had elevated serum titers of mouse IgG/human kappa after four immunizations. Again, in general, all mice of line 9B2-58 expressed high IFN-α specific mouse IgG, while only some mice of the others lines expressed IFN-α specific mouse IgG post immunization.

Example 4

Analysis of Somatic Mutations in Chimeric Antibodies

In this example, the number of somatic mutations that occurred in anti-TT chimeric antibodies from the 9B2-58 transgenic mouse strain was analyzed, as well as the number of somatic mutations that occurred in chimeric antibodies from HuMab mice (which express both chimeric and fully human antibodies).

9B2-58 Transgenic Mice

Based on cDNA sequencing, the antibodies made by the anti-TT hybridomas generated from immunization of 9B2-58 transgenic mice, as described in detail in Example 3 above, were further characterized for their $V_H$ and $J_H$ usage and for which heavy chain isotype was present. Additionally, the number of somatic mutations occurring at the DNA level and at the amino acid level was determined for the $V_H$ segment only (not the D or $J_H$ segments). The results are summarized in Table 4 below:

TABLE 4

Sequence Analysis of Antibodies from TT Immunized 9B2 Mice

| Clone Name | $V_H$ | $J_H$ | SM (DNA) | SM (AA) | HC Isotype |
|---|---|---|---|---|---|
| 43H7C10* | 3-30.3 | 4 | 15 | 9 | mIgG2b |
| 43C4E8* | 3-30.3 | 4 | 18 | 8 | mIgG2b |
| 41A7B2* | 3-30.3 | 4 | 15 | 8 | mIgG2b |
| 7G7A9** | 3-30.3 | 4 | 5 | 3 | mIgG2b |
| 14D6G4** | 3-30.3 | 4 | 5 | 3 | mIgG2b |
| 24F10A8** | 3-30.3 | 4 | 5 | 3 | mIgG2b |
| 40G8F2** | 3-30.3 | 4 | 5 | 3 | mIgG2b |
| 50C1G4 | 4-34 | 4 | 17 | 7 | mIgG1 |
| 49A1A6 | 4-34 | 4 | 17 | 7 | mIgG1 |
| hu anti-TT | 3-33 | 4b | 13 | 10 | h IgG1 |
| chi anti-TT | 3-33 | 4b | 13 | 10 | mIgG2a |

SM = somatic mutations; HC = heavy chain
*indicates antibodies determined to share the same light chain
**indicates antibodies determined to share the same light and heavy chains With regard to $V_H$ region usage, it should be noted that although the 9B2-58 transgenic strain comprises different $V_H$ regions than those in the HuMab mouse used to raise the human anti-TT antibody, the 3-30.3 and 3-33 $V_H$ regions are similar, differing by only 2 amino acids. Thus, for several of the hybridomas, TT immunization selected similar $V_H$ regions in the 9B2-58 transgenic strain as the $V_H$ region used in a human anti-TT antibody raised in the HuMab mouse.

With regard to heavy chain isotype determination, since the transgene inserted into the 9B2-58 strain contains only the mouse IgM constant region, all of the chimeric antibodies that contain a human variable region and a mouse IgG2b or IgG1, as observed herein, were produced through trans-switching from the transgene to various endogenous mouse constant regions.

With regard to somatic mutations, at the DNA level, several of the antibodies from the 9B2-58 transgenic strain displayed greater numbers of somatic mutations than the human anti-TT antibody from the HuMab mouse. Moreover, chimeric antibodies with higher affinities for TT also contained more somatic mutations than other anti-TT antibodies identified from the same transgenic mouse. Although at the amino acid level, the chimeric antibodies from the 9B2-58 transgenic strain did not exhibit more somatic mutations than the human anti-TT antibody from the HuMab mouse (due to the degeneracy of the genetic code), the increased number of somatic mutations observed at the DNA level for several of the chimeric antibodies derived from the 9B2-58 transgenic strain supports the position that expression in transgenic mice of chimeric antibodies that contain a host constant region can lead to increased somatic mutations rates in the chimeric antibodies.

HuMab Mice

The data described above for the 9B2-58 strain with regard to somatic mutations is consistent with observations that have been made about somatic mutation rates in the HuMab mouse, which express fully human antibodies but which also may express chimeric antibodies due to trans-switching between the human heavy chain transgene and the endogenous mouse constant region.

For example, HuMab mice (HCo12/7 and HCo12 mice) were immunized with a cell surface receptor and the spleens were isolated and fused according to standard hybridoma techniques. Eight anti-receptor antibodies were isolated from the fusion mixture and sequenced. Three of the antibodies were chimeric in nature, consisting of human VDJ regions linked to a mouse IgG2b constant region. The remaining five antibodies were fully human antibodies. cDNA sequence analysis of all the heavy chain variable regions showed that the chimeric and human antibodies used different variable region recombinations, and the chimeric antibodies had higher somatic mutations at the DNA level than the fully human antibodies and correlating higher amino acid differences. As for the 9B2-58 mice described above, the somatic mutation quantitation was determined for the $V_H$ segment only (not the D or $J_H$ segments). The results are summarized below in Table 5:

TABLE 5

Sequence Analysis of Human and Chimeric Antibodies from HuMab Mice

| Clone Name | $V_H$ | $D_H$ | $J_H$ | SM (DNA) | SM (AA) | HC Isotype |
|---|---|---|---|---|---|---|
| Chimeric 1 | 3-23 | 3-9 | 4a | 16 | 12 | mIgG2b |
| Chimeric 2 | 3-23 | 3-9 | 4b | 16 | 13 | mIgG2b |
| Chimeric 3 | 3-23 | 3-9 | 4b | 16 | 12 | mIgG2b |
| Human 1 | 3-30.3 | nd | 4b | 8 | 6 | hIgG1 |
| Human 2 | 3-30.3 | nd | 4b | 7 | 7 | hIgG1 |

TABLE 5-continued

Sequence Analysis of Human and Chimeric Antibodies from HuMab Mice

| Clone Name | $V_H$ | $D_H$ | $J_H$ | SM (DNA) | SM (AA) | HC Isotype |
|---|---|---|---|---|---|---|
| Human 3 | 3-33 | 3-10 | 3b | 2 | 2 | hIgG1 |
| Human 4 | 3-33 | 7-27 | 4b | 2 | 2 | hIgG1 |
| Human 5 | 3-33 | 5-5 | 3b | 6 | 4 | hIgG1 | nd = not determined, SM = somatic mutation; HC = heavy chain

In another set of experiments, HuMab mice (HCo12/7) immunized with a soluble cytokine and the spleens were isolated and fused according to standard hybridoma techniques. Six anti-cytokine antibodies were isolated from the fusion and sequenced. Five of the antibodies were chimeric in nature consisting of human VDJ regions linked to a mouse IgG2a and IgG2b constant region. The remaining antibody was fully human antibodies. cDNA sequence analysis of all the heavy chain variable regions showed that the chimeric antibodies and human antibody used similar and different variable region recombinations and that the chimeric antibodies again had higher somatic mutations at the DNA level than the fully human antibody and correlating higher amino acid differences. Furthermore, the chimeric antibody #5 had a higher blocking efficiency than the fully human antibody #1 in functional blocking assays. The results are summarized below in Table 6:

TABLE 6

Sequence Analysis of Human and Chimeric Antibodies from HuMab Mice

| Clone Name | $V_H$ | $D_H$ | $J_H$ | SM (DNA) | SM (AA) | HC Isotype |
|---|---|---|---|---|---|---|
| Chimeric 1 | 3-30.3 | nd | 4b | 21 | 13 | mIgG2b |
| Chimeric 2 | 3-30.3 | 7-27 | 4b | 8 | 7 | mIgG2a |
| Chimeric 3 | 1-69 | nd | 4b | 9 | 6 | mIgG2a |
| Chimeric 4 | 1-69 | nd | 4b | 9 | 6 | mIgG2a |
| Chimeric 5 | 1-69 | nd | 4b | 25 | 15 | mIgG2a |
| Human 1 | 1-69 | nd | 4b | 7 | 7 | hIgG1 | nd = not determined, SM = somatic mutation; HC = heavy chain

Thus, the results from the experiments described above for HuMab mice immunized with two different antigens support the position that expression in transgenic mice of chimeric antibodies, that contain a host constant region, can lead to increased somatic mutations in the chimeric antibodies, as compared to fully human antibodies expressed in the transgenic mice.

Example 5

Generation of a Second Transgene for Expression of Chimeric Antibodies

In this example, another transgene for expressing chimeric antibodies in mice was created, referred to as HCo26. The HCo26 transgene differs from the 9B2 transgene described in Example 1 in that the 9B2 transgene contains only the mouse IgM constant region whereas the HCo26 transgene contains all of the mouse constant region coding sequences.

HCo26 consists of three imbricate DNA fragments that contain unrearranged human V, D and J regions and the mouse IgH locus from the 5' Eμ enhancer through the identified 3' DNase hypersensitive sites and origin of replication (Zhou, et al. (2002) *Proc. Natl. Acad. Sci. USA* 99:13693-13698). The construction of the HCo26 transgene is illustrated schematically in FIG. 1.

The first of the three fragments is the approximately 57 kb NotI-SalI fragment from clone 9B2 of phVDJ-mEM (described in Example 1) containing unrearranged human heavy chain VDJ segments linked to the mouse J-μ enhancer region, μ switch region and μ coding region. Another fragment consists of the approximately 140 kb NgoMIV-NotI fragment of the previously described B20 BAC, which contains the mouse J-μ enhancer, mouse μ constant coding regions and the intervening mouse genomic regions through the mouse γ2b coding constant region. As the mouse J-μ enhancer and mouse μ switch regions make up part of the 9B2 fragment, these regions are part of the overlapping regions of 9B2 and the B20 fragment. Another fragment consists of the approximately 180 kb NotI-NotI fragment of C22 BAC, which consists of the mouse γ2b coding constant region and the intervening mouse genomic regions through the DNase hypersensitive sites 3' of the mouse cc coding regions to the endogenous NotI site found in the C22 BAC fragment. The mouse γ2b coding regions make up the overlapping regions of the B20 and the C22 BAC fragments.

The approximately 57 kb NotI-SalI fragment from clone 9B2 of phVDJ-mEM was released from the vector, as was the approximately 140 kb NgoMIV-NotI fragment of the B20 BAC and the approximately 180 kb NotI-NotI fragment of C22 BAC. Each was then isolated by PFGE. An agarose gel slice with each of the fragments was excised and the agarose was digested with β-agarase (commercially obtained from Takara) according to the manufacturer's protocol. The three fragments were then mixed to a 1:1:1 stoichiometry and the mixture is referred to as HCo26. The HCo26 DNA mixture was then micro-injected (by standard methods) into fertilized oocytes. DNA was injected into JHD (KCo5) (JHD+/+ CMD−/−, JKD+/+, KCo5+) mice. Potential founder mice were screened for the 9B2 transgene by PCR with DMTM79 and DMTM80 using tail DNA as template. Two different founder mice, HCo26-05 and HCo26-16, tested positive for the 9B2 transgene on the JHD+/+, CMD−/−, JKD+/+, KCo5+ strain background. Furthermore, Southern Blot analysis of genomic DNA from the HCo26-05 mouse had 2 positive hybridizing BamHI bands with an approximately 1 kb probe at the 3' end of the C22 fragment. One band represents the 3' end of the endogenous mouse IgH locus, while the other represents the integration of the C22 fragment into the mouse genome in a random manner.

Founder mice positive for the HCo26 transgenes were then bred to JHD (KCo5) mice (JHD+/+, CMD−/−, JKD+/+, KCo5+/+ mice) and genotyped for 9B2, JHD, CMD, JKD and KCo5. HCo26-05 founder transmitted the HCo26 transgene to several offspring.

These HCo26 founders are crossed to JHD (KCo5) mice to generate distinct stable HCo26 lines. HCo26 positive mice are tested for pre-immune levels of mouse IgM/human kappa and mouse IgG/human kappa as described in the examples above. Furthermore, HCo26 mice can be immunized with TT or other antigens and titered for mouse IgG/human kappa and antigen+/mouse IgG levels as described in the examples above.

Example 6

Conversion of Chimeric Antibodies to Fully Human Antibodies and Comparison Thereof To convert a chimeric antibody to a fully human antibody, cDNA of the variable regions (comprising the rearranged human VDJ segments) of the heavy chain and light chain are isolated and sequenced. Total RNA is obtained from hybridoma cell pellets secreting the desired antibody by utilizing Qiagen RNeasy Mini Kit. cDNA is then prepared using the 5' RACE protocol utilizing Clontech SMART RACE cDNA Amplification Kit. Variable regions of each antibody are then amplified using a 3' primer specific for the mouse constant region paired with the 5' RACE universal primer mix. PCR products containing the variable regions are then cloned into the Invitrogen TOPO TA DNA sequencing vectors. Mini-preped DNA samples are prepared and DNA sequenced. DNA sequences are then trimmed to include only the variable region of the desired antibody. Variable regions of the antibody are then matched to the germline human V(D)J regions used to generate the 9B2 mice to ensure they are of transgene origin and thus of human origin Variable regions are also compared with mouse variable regions to rule out any mouse derived variable regions. cDNA sequences are compared with the N-terminal amino acid sequencing and mass spec analysis of the desired antibody to ensure the correct cDNA sequence is obtained.

Once the correct cDNA sequence is obtained, primers are synthesized to independently PCR the coding regions of the heavy and light chain variable regions. Furthermore, appropriate restriction sites are added in frame to the coding regions to allow for cloning of the coding variable regions directly into expression vectors that already encode for a human constant region. Thus, a variable region (light or heavy chain) is inserted into an expression vector such that the appropriate variable region sequences are operatively linked to the appropriate human constant region sequence, as well as to transcriptional and translational control sequences. An antibody heavy chain gene and an antibody light chain gene can be inserted into separate vectors or, more typically, both genes are inserted into the same expression vector. An expression vector can be used that already encodes heavy chain constant and light chain constant regions of the desired isotype such that the $V_H$ segment is operatively linked to the $C_H$ segment(s) within the vector and the $V_L$ segment is operatively linked to the $C_L$ segment within the vector. Non-limiting examples of suitable expression vectors for expressing fully human antibodies include the pIE family of vectors as described in U.S. Patent Application No. 20050153394 by Black.

For expression of the light and heavy chains, the expression vector(s) encoding the heavy and light chains is transfected into a host cell by standard techniques. Preferred mammalian host cells for expressing the recombinant antibodies of the invention include Chinese Hamster Ovary (CHO cells), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The general methodology described above for converting a chimeric antibody to a fully human antibody was used to convert an anti-TT mAb raised in the 9B2-58 strain of transgenic mouse to a fully human antibody. More specifically, the heavy chain and light chain variable regions of the anti-TT antibody 43H7C10 (described in Example 4) (a chimeric antibody consisting of a human VDJ variable region operatively linked to a mouse gamma 2b constant region and paired with a fully human Kappa light chain) were cloned into expression vectors such that the human heavy chain variable region and light chain variable region sequences were operatively linked to sequences encoding a human gamma 1 constant region and a human Kappa constant region, respectively, to allow for the preparation of a recombinant fully human 43H7C10 antibody. The 43H7C10 human heavy chain and light chain variable region sequences also were cloned into expression vectors such that they were operatively linked to sequences encoding the mouse gamma 2a constant region and human Kappa constant regions, respectively, to allow for the preparation of a recombinant chimeric 43H7C10 antibody. Expression vectors encoding the recombinant fully human 43H7C10 antibody and the recombinant chimeric 43H7C10 antibody were transfected by standard techniques into CHO cells and both forms of the 43H7C10 antibody protein was produced independently and purified using standard protein purification methods. The two purified antibody proteins were then used in a BIACORE experiment to determine and compare the affinity to TT, as well as on-rates and off-rates, by standard methodologies. For comparison, 1D6 (a fully human anti-TT antibody originally raised in a HuMab Mouse®) was also produced as a fully human antibody as well as a recombinant chimeric mouse IgG/human kappa antibody (both expressed in CHO cells). Results of the affinity, on-rate and off-rate comparison are shown in Table 7 below.

TABLE 7

Binding Kinetics of Chimeric vs. Human Anti-TT Antibodies

| Clone Name | Antibody form | Affinity (nM) | On-rate (1/Ms) × 10$^4$ | Off-rate (1/s) × 10$^4$ |
|---|---|---|---|---|
| 43H7C10 | Chimeric | 17.9 | 8.9 | 15.9 |
| 43H7C10 | Fully human | 11.7 | 4.8 | 5.6 |
| 1D6 | Chimeric | 66.9 | 29.1 | 19.4 |
| 1D6 | Fully human | 46.3 | 25.1 | 11.6 |

This data demonstrates that a chimeric anti-TT antibody raised in a transgenic mouse of the invention can be recombinantly reconfigured to a fully human antibody form and still maintain its binding properties toward its target antigen. In fact, the recombinant fully human form of the antibody exhibits somewhat higher binding affinity for the target antigen than the recombinant chimeric form. Furthermore, both the chimeric and fully human recombinant forms of the 43H7C10 antibody exhibit higher binding affinity for the target antigen than the fully human 1D6 mAb raised in a HuMab Mouse®, thereby demonstrating that the transgenic mice of the invention can allow for the preparation of a fully human antibody against a target of interest that has higher affinity for the target than a fully human antibody raised in a HuMab Mouse®.

We claim:

1. A transgene construct comprising a 9B2 transgene.
2. The construct of claim 1, which comprises a HCo26 transgene.
3. A transgenic mouse whose genome comprises the transgene construct of claim 1.
4. A method of making a chimeric antibody specific for an antigen of interest comprising immunizing the transgenic mouse of claim 3 with the antigen of interest and obtaining from the mouse a chimeric antibody specific for the antigen of interest.
5. The method of claim 4, further comprising isolating from the mouse a nucleic acid encoding a chimeric immunoglobulin (Ig) heavy chain and replacing nucleic acid encoding the mouse Ig heavy chain constant region with nucleic acid encoding a human Ig heavy chain constant region to convert the nucleic acid encoding the chimeric Ig heavy chain to a nucleic acid encoding a human Ig heavy chain, and expressing the human Ig heavy chain.

* * * * *